(12) United States Patent
Polichar et al.

(10) Patent No.: US 6,205,199 B1
(45) Date of Patent: Mar. 20, 2001

(54) PIXEL-CORRELATED, DIGITAL X-RAY IMAGING SYSTEM

(75) Inventors: Raulf M. Polichar; Scott T. Smith, both of San Diego; William B. Thompson, Carlsbad; Aaron R. Polichar, San Diego, all of CA (US)

(73) Assignee: Science Applications International Corporation, San Diego, CA (US)

( * ) Notice: Subject to any disclaimer, the term of this patent is extended or adjusted under 35 U.S.C. 154(b) by 0 days.

(21) Appl. No.: 09/225,185

(22) Filed: Jan. 4, 1999

Related U.S. Application Data

(60) Continuation-in-part of application No. 09/076,604, filed on May 11, 1998, now Pat. No. 5,909,478, which is a division of application No. 08/773,483, filed on Dec. 23, 1996, now Pat. No. 5,828,726, which is a continuation of application No. 08/494,251, filed on Jun. 23, 1995, now Pat. No. 5,608,774.

(51) Int. Cl.[7] .................................................. H05G 1/64
(52) U.S. Cl. ........................................ 378/98.8; 378/98.2
(58) Field of Search .............................. 378/98, 98.2, 98.8

(56) References Cited

U.S. PATENT DOCUMENTS

| | | | |
|---|---|---|---|
| 4,383,327 | 5/1983 | Kruger | 378/19 |
| 4,593,337 | 6/1986 | Mouyen | 378/98.8 |
| 4,612,660 | 9/1986 | Huang | 378/44 |
| 4,736,239 | * 4/1988 | Sprague et al. | 348/717 |
| 4,982,283 | * 1/1991 | Acampora | 348/410 |
| 5,127,032 | 6/1992 | Lam et al. | 378/98.3 X |
| 5,235,191 | 8/1993 | Miller | 378/98.3 X |
| 5,434,418 | 7/1995 | Schick | 378/98.8 |
| 5,452,337 | 9/1995 | Endo et al | 378/4 |
| 5,454,022 | 9/1995 | Lee et al. | 378/98.8 |
| 5,550,380 | 8/1996 | Sugawara et al. | 378/98.3 X |
| 5,584,292 | 12/1996 | Cheung | 378/98.3 X |
| 5,608,774 | 3/1997 | Polichar et al. | 378/98.8 |
| 5,828,726 | 10/1998 | Polichar et al. | 378/98.2 |
| 5,909,478 | 6/1999 | Polichar et al. | 378/98.2 |

FOREIGN PATENT DOCUMENTS 0429977   11/1990   (EP) .

OTHER PUBLICATIONS

Street, et al., "Charge–Coupled Devices and Solid State Optical Sensors IV", *SPIE*, 2172:144–154 (Feb. 7–8, 1994).
Street, et al., "Amorphous Silicon Arrays Develop a Medical Image", *IEEE*, pp: 38–42 (Jul. 1993).
Tannas, "Evolution of Flat–Panel Displays", *Proceedings of the IEEE*, 82:4, pp. 499–509 (Apr. 1994).
Antonuk, et al., "Considerations for High Frame Rate Operation of Two–Dimensional a–Si:H Imaging Arrays", *Materials Research Society Symposium Proceedings*, 297:945–950 (1993).
VIDISCO, Ltd., Sales Brochure for "A–500E Portable Video Based X–Ray Inspection System" (1994).

* cited by examiner

*Primary Examiner*—David V. Bruce
(74) *Attorney, Agent, or Firm*—Fitch, Even, Tabin & Flannery

(57) ABSTRACT

A portable, self-contained, electronic radioscopic imaging system uses a pulsed X-ray source, a remote X-ray sensor, and a self-contained, display and controller unit to produce, store, and/or display digital radioscopic images of an object under investigation. An X-ray image sensor configured to spatially sense X-ray radiation pulses includes a pixel clock generator, an integrating CCD camera imager operating in a progressive scan mode providing a discrete pixel readout cycle of sensed X-ray radiation pulses, a sample and hold circuit for sampling the discrete pixel readout responsive to the pixel clock, and an analog to digital converter for digitizing each pixel as the discrete pixel readout is sampled. A digital video transmission system controller board controls the X-ray source for acquiring digitized samples from the X-ray image sensor. The digital video transmission system has a buffer memory for storing digitized pixels received from the analog to digital converter, and is further provided with a serial interface driver for transmitting the digitized pixels. An image processor receives the digitized pixels transmitted by the serial interface driver of the controller for generating a radioscopic image from the digitized pixels.

22 Claims, 12 Drawing Sheets

PIXEL CORRELATED DIGITAL IMAGING SYSTEM

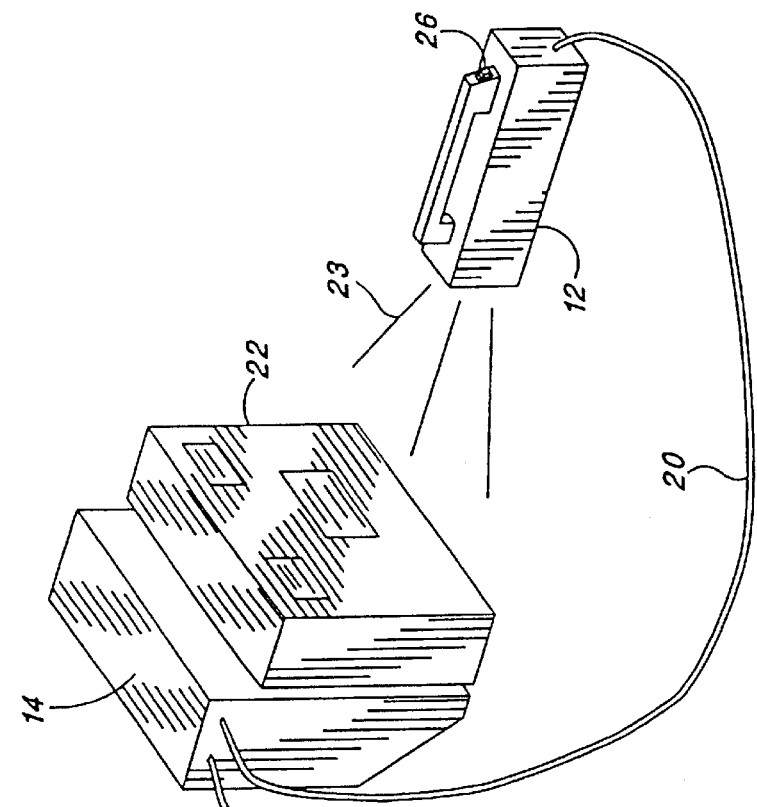
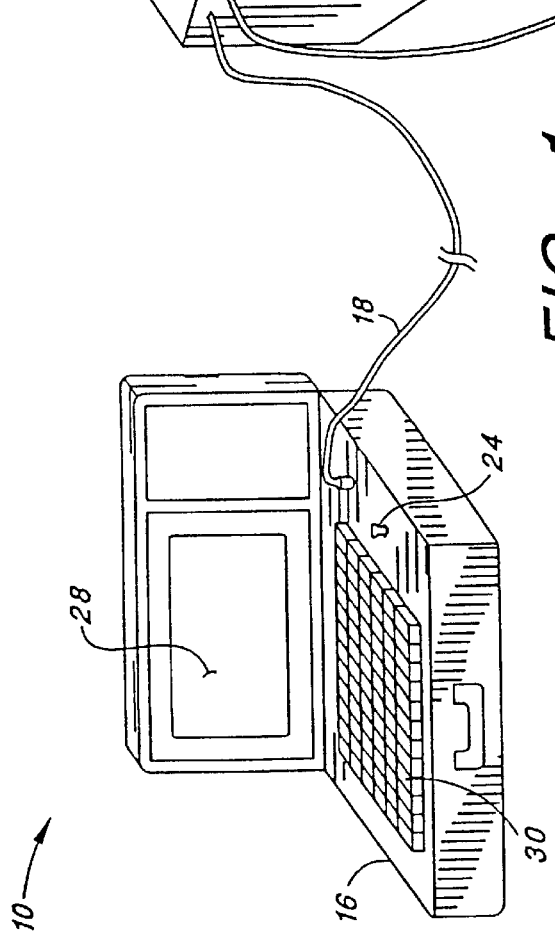
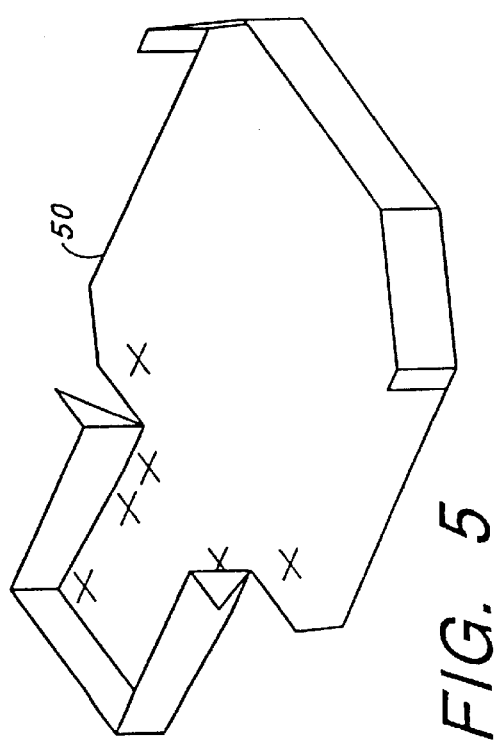
FIG. 1
FIG. 5

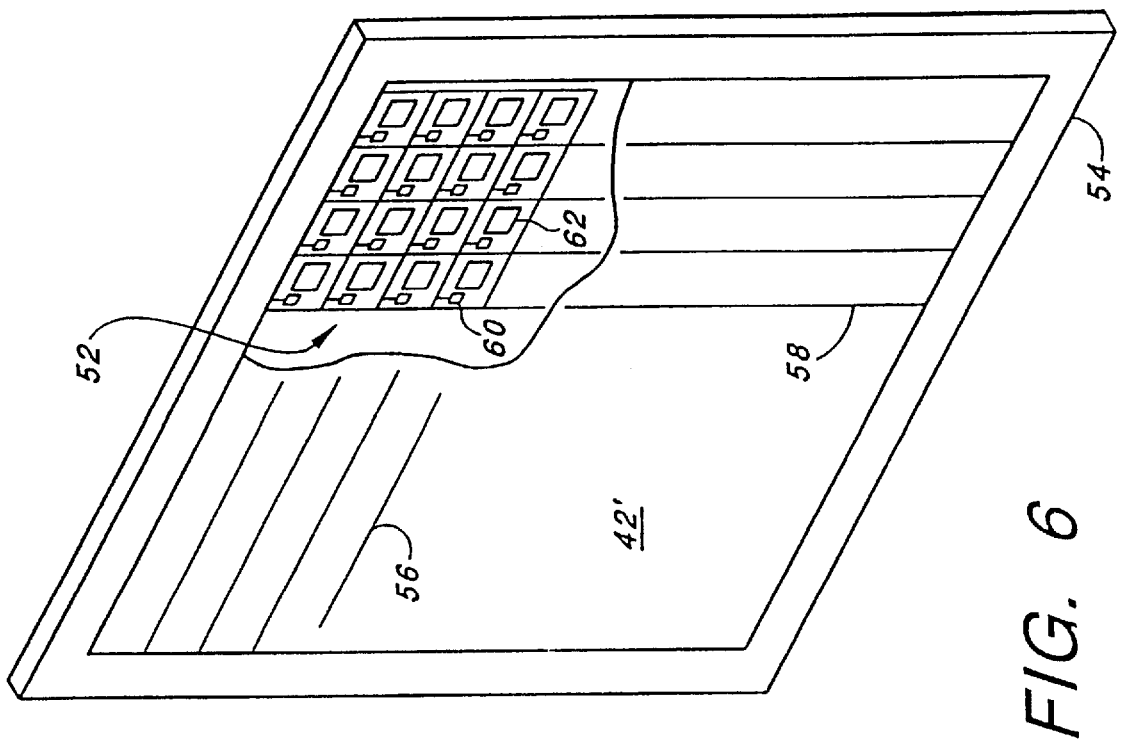
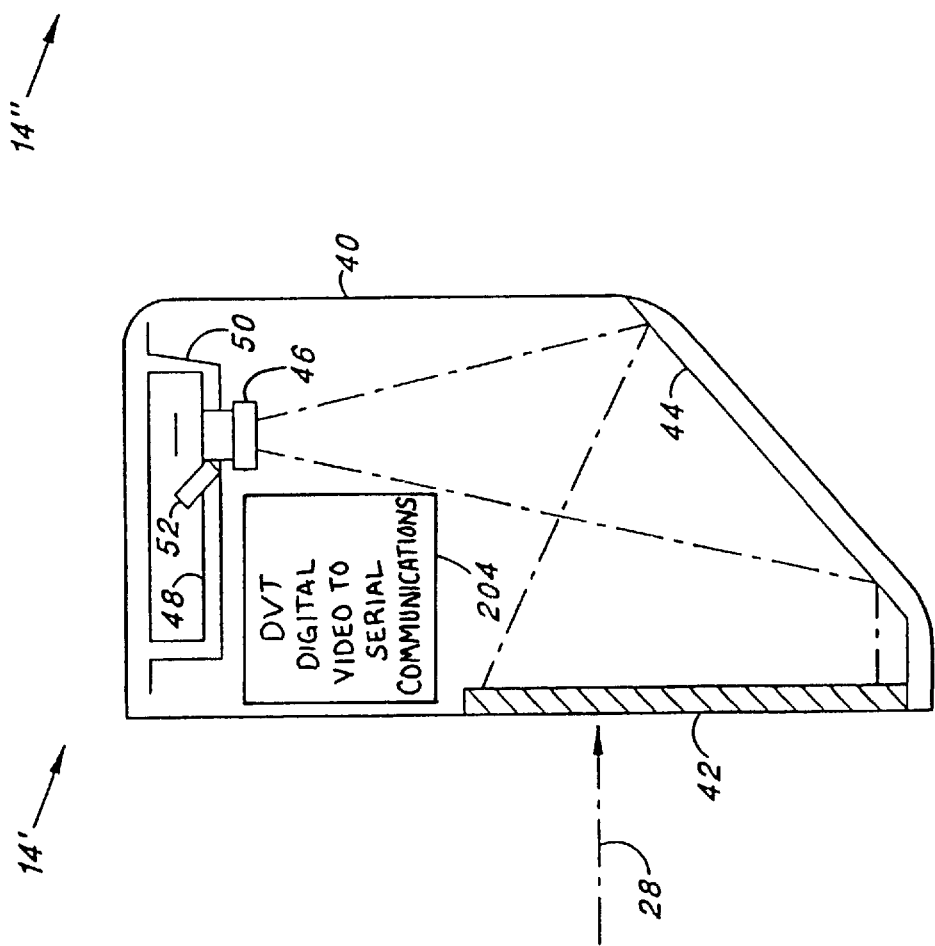

PIXEL-CORRELATED, DIGITAL X-RAY IMAGING SYSTEM

CROSS-REFERENCE TO RELATED APPLICATIONS

This application is a continuation-in-part of application Ser. No. 09/076,604, filed May 11, 1998, now U.S. Pat. No. 5,904,478, which is a divisional application of Ser. No. 08/773,483, filed Dec. 23, 1996, now U.S. Pat. No. 5,828,726, which is a continuation of application Ser. No. 08/494,251, filed Jun. 23, 1995, now U.S. Pat. No. 5,608,774.

BACKGROUND OF THE INVENTION

The present invention relates to a portable, self-contained, X-ray apparatus that digitally acquires, processes, displays, stores, and/or transmits electronic radioscopic images of sealed packages, containers and other objects, including patients, on location for security, customs, medical, and other non-destructive and non-invasive purposes. More particularly, the present invention provides an improved clocking and digitization system for use with a portable X-ray radioscopic imaging system to enhance the spatial quality and contrast sensitivity of an on-chip integrated image of an otherwise conventional charge-coupled device (CCD) camera by employing the direct clocking of pixels and correlated digitization of their signals within the camera head.

Some of the general concerns and problems associated with portable, digital X-ray apparatus for producing, storing and displaying electronic radioscopic images are set forth in U.S. Pat. No. 5,608,774, incorporated herein by reference. The '774 patent sets forth a system in which a pulsed X-ray source transmits a burst of narrow pulses of X-rays at the object being investigated at a low repetition rate. The X-ray sensor utilizes an X-ray scintillating screen in combination with either an integrating CCD camera, or an active matrix of thin film transistors and sample-and-hold photodiodes, to produce an integrated signal representative of the accumulated number of X-ray pulses that are sensed in a given pixel area of the scintillating screen. The self-contained display and controller unit utilizes digital signal processing within an enhanced portable computer, including a flat solid state display panel and associated drive circuitry, in order to display the full dynamic range and resolution of the sensor. A modem allows the digitized image to be sent to a remote location where the exact same image can be recreated for analysis by off-site experts, e.g., via an internal ethernet LAN, intranet, or internet connection.

Presently, an analog CCD Video camera puts out standard RS-170 waveform. Each line must be read out in approximately 63.5 microseconds in an interlaced format. A conventional CCD camera employing an analog video readout is modified to suppress normal blanking and readout of CCD until sufficient flux is integrated onto chip to provide a full scale output signal. At this point, the system then waits until the beginning of the next active interlaced field (odd or even) and then reads out the following two successive fields to a digitizer remotely located at the computer display unit. It would be desirable therefore, to address the specific problems associated with analog CCD Video cameras to provide improved signal to noise and resolution for the CCD camera over currently used video based X-ray imagers.

There are many instances in the medical, security or customs field when it is necessary to examine or inspect, in a non-invasive way, a patient, animal, or other living organism; or to examine and inspect, in a non-destructive way, the contents of a closed package, box, suitcase, or other container. For example, customs departments are routinely charged with the responsibility of inspecting the contents of incoming packages to make sure such packages do not contain explosives, drugs or other contraband. Similarly, terrorists, criminals, or other enemies frequently carry out their criminal acts of terrorism or war by planting bombs in sealed containers or packages, and then sending the sealed containers/packages to the intended victims, e.g., through the mail, or planting the sealed container/packages at the desired target, e.g., by leaving a locked suitcase or a sealed box containing a bomb in a busy public transportation terminal. When security personnel encounter suspicious packages or other containers being sent through the mail, or left at public transportation terminals, or other locations, they must perform a careful inspection of such containers to ascertain their contents.

When suspicious containers, such as suitcases, sealed boxes/packages are discovered, they generally must be examined or inspected on location in a non-destructive manner. If the non-destructive examination reveals the presence of explosives (e.g., a bomb) or contraband (e.g., drugs), then the container and its contents must be safely disposed of. If, on the other hand, the examination reveals the absence of explosives or contraband, then the container may be handled in a normal manner, i.e., forwarded on to its owner or addressee.

Unfortunately, the process used to examine or inspect a suspicious sealed box, package, suitcase or other container must not trigger any bomb that may be concealed inside. Thus, for example, as a safety precaution, the suspicious container may not be opened because such opening may trigger any bomb contained therein. Similarly, the suspicious container may not be moved because such movement could likewise trigger a hidden bomb. Further, the suspicious container may not be examined with high doses of radiation because such radiation, if significantly greater than normal background radiation, could also trigger a hidden bomb. What is needed, therefore, is a non-invasive technique for inspecting the contents of a suspicious container without requiring that the container be opened, moved, or subjected to high levels of radiation.

Heretofore, suspicious containers of the type referenced above have been examined using portable, generally low power, X-ray generators and highly sensitive X-ray film as a detector, with many attendant problems. For example, the film used with such conventional film-based radiography systems has a poor shelf life in the environment typical to field inspections, which means that its sensitivity may vary considerably. The operator must then go back to the object under test for each image taken until the correct exposure and orientation is obtained. Once such image is taken, it must then be processed with a portable chemical laboratory with the attendant delays of such efforts.

It is also known in the art to improve the conventional film-based radiography systems by adapting certain types of industrial imaging systems as an image detection system to overcome some of the field problems. Such systems typically use intensified, low-light level cameras to record the image, and then conventional cathode ray tube (CRT) monitors to display the resulting X-ray images. Unfortunately, such systems are bulky and poorly suited for portable applications. Further, the CRT displays do not always provide the contrast needed to readily see the X-ray image in bright ambient light conditions. Further, while some limited image enhancement techniques have been applied to such existing systems, the output image is still simply a real-time analog CRT image.

The shortcomings of analog approaches are introduced by the constraints of the standard RS-170, video timing and waveforms as well as the need to filter the outputs of the discrete pixel outputs into a continuous waveform which must then be redigitized at the end of a long cable. This multiple conversions between digital and analog signals introduces a loss of modulation in the higher spatial frequencies which causes a corresponding loss of contrast in the reproduced images especially for the finer structure in the image. Moreover, putting the analog to digital converter at the computer requires that the analog signal be transmitted over a long cable with attendant loss of high frequency information further reducing the contrast of the fine structure in the image.

SUMMARY OF THE INVENTION

Broadly, and in general terms, a goal of the present invention is to provide a completely digital system capable of recording and digitizing the individual X-ray image data, including the ability to store and retrieve that data onto a suitable storage medium, such as a hard disk of a portable computer, and using such portable computer as a controller for selectively displaying the image in a way that reveals the full dynamic range and resolution of the sensor, and/or transmitting the image to remote locations (when necessary) via a modem, or ethernet connection, for evaluation by experts who are not on site.

The present invention addresses the above and other goals by providing a portable, self-contained, electronic radioscopic imaging system. The system is made up of three main subsystems: (1) a pulsed X-ray source, (2) a remote X-ray sensor, or "imager", and (3) a self-contained, display and controller unit, or "display/control unit." The pulsed X-ray source transmits narrow pulses of X-rays at the object being investigated at a low repetition rate. The X-ray sensor or imager utilizes a scintillating screen that produces flashes of light when impinged by an X-ray in combination with either an integrating CCD camera, or an active matrix of thin film transistors and thin film sample-and-hold photo-diodes, to produce an integrated signal that represents the sum of a prescribed number of flashes of radiation that pass through the object in a given pixel area. The self-contained display and control unit utilizes digital signal processing within an enhanced portable computer, including a solid-state flat panel display and associated drive circuitry, in order to display to an operator the full dynamic range and resolution of an image-capturing novel sensor utilized within the imager. A modem or an ethernet connection further permits the digitized image to be sent to a remote location where the exact same image can be recreated for analysis by off-site experts.

The purpose of the invention embodied in the additional digital imaging embodiment described below is to improve the image quality of an integrating CCD camera used for digital radioscopic imaging. Conventional CCD video cameras operate in a mode which samples the light from each pixel in a line and creates a filtered analog signal in the form of a standard television (RS-170) like waveform. In many radiographic systems, this type of video signal is then redigitized and stored on a computer or special purpose imager processor with a subsequent loss in modulation and noise performance for the higher spatial frequencies. The portable digital radiographic system described herein, on the other hand, operates the CCD in an extended, on-chip integration period to collect the light generated by a series of flashes of a small generator until sufficient flux has been recorded to produce a sensitive electronic radioscopic image. The camera then goes through a single read out cycle and reads out the stored charge signal to a closely located digitizer.

The present invention improves the quality of the resulting image in two distinct areas. This camera operates in a discrete pixel mode through out all of its readout cycle digitizing each pixel as the signal is sampled and sends the resulting digital image to the computer. The major advantages of this process are that since the information from each pixel is treated independently and not filtered into an analog waveform, the higher spatial frequencies are better preserved making the image appear sharper. Secondly, since the speed of the single readout is no longer determined by standard video refresh rates, the amplifiers and digitizers can be operated in a more favorable noise situation greatly extending the dynamic range of the gray scale of the image.

The use of transmitted digital (either as parallel words or serialized data strings) is much less subject to noise pickup and loss of high frequency data. The system is designed to use the same type of CCD chips found in low cost video cameras and digital still cameras and one need not resort to specialized scientific quality imaging chips to gain the stated improvements in performance. In this approach, one could use cameras of differing resolution with the same controller by simply adjusting the software to redefine the number of pixels per line and lines per frame. It also allows all cameras to be read out in progressive scan rather than using interlaced video fields which further simplifies the organization of the data after it enters the computer.

It is an object of the present invention to overcome the shortcomings of prior art analog CCD Video image processing systems.

It is another object of the invention to provide a system and a method for processing a digital image.

It is further object of the invention to provide a pixel-correlated digital imaging system.

It is yet another object of the invention to provide a system for processing a radioscopic image of an object under investigation.

In a preferred embodiment, an X-ray image sensor configured to spatially sense X-ray radiation pulses includes a pixel clock generator, an integrating CCD camera imager operating in a progressive scan mode providing a discrete pixel readout cycle of sensed X-ray radiation pulses, a sample and hold circuit for sampling the discrete pixel readout responsive to the pixel clock, and an analog to digital converter for digitizing each pixel as the discrete pixel readout is sampled. A digital video transmission system controller board controls the X-ray source for acquiring digitized samples from the X-ray image sensor. The digital video transmission system has a buffer memory for storing digitized pixels received from the analog to digital converter, and is further provided with a serial interface driver for transmitting the digitized pixels. A remote image processor receives the digitized pixels transmitted by the serial interface driver of the controller for generating a radioscopic image from the digitized pixels.

Briefly summarized, the present invention relates to a pixel clock generator for use with a pixel-correlated digital imaging system, which includes an imager operating in a progressive scan mode providing a discrete pixel readout cycle. A sample and hold circuit samples the discrete pixel readout responsive to the pixel clock, and an analog to digital converter is provided for digitizing each pixel as the discrete pixel readout is sampled. A controller includes a buffer memory for storing digitized pixels received from the analog to digital converter, and an image processor is in communication with the controller for generating an image from the digitized pixels. A serial communications link between the buffer memory and the image processor facilitates remote communications between the controller and the image processor. The controller is further equipped with a serial interface driver for transmitting the digitized pixels to the image processor via the serial communications link.

BRIEF DESCRIPTION OF THE DRAWINGS

The above and other aspects, features and advantages of the present invention will be more apparent from the following more particular description thereof, presented in conjunction with the following drawings wherein:

FIG. 1 depicts the three main subsystems of the imaging system of the present invention as it is used to form a radiographic image of a package under investigation;

FIG. 3 illustrates a CCD camera version of the X-ray sensor that may be used with some embodiments of the system of FIGS. 1 and 2;

FIG. 5 is a perspective view of a special shield that is used to shield the CCD camera included in FIG. 3;

FIG. 6 depicts a TFT flat panel amorphous silicon X-ray sensor that may be used with other embodiments of the system of FIGS. 1 and 2;

FIG. 12 is a block diagram representing a fully digital imaging system in accordance with the pixel correlated embodiment of the present invention;

Corresponding reference characters indicate corresponding components throughout the several views of the drawings.

DETAILED DESCRIPTION OF THE INVENTION

Figure 2:
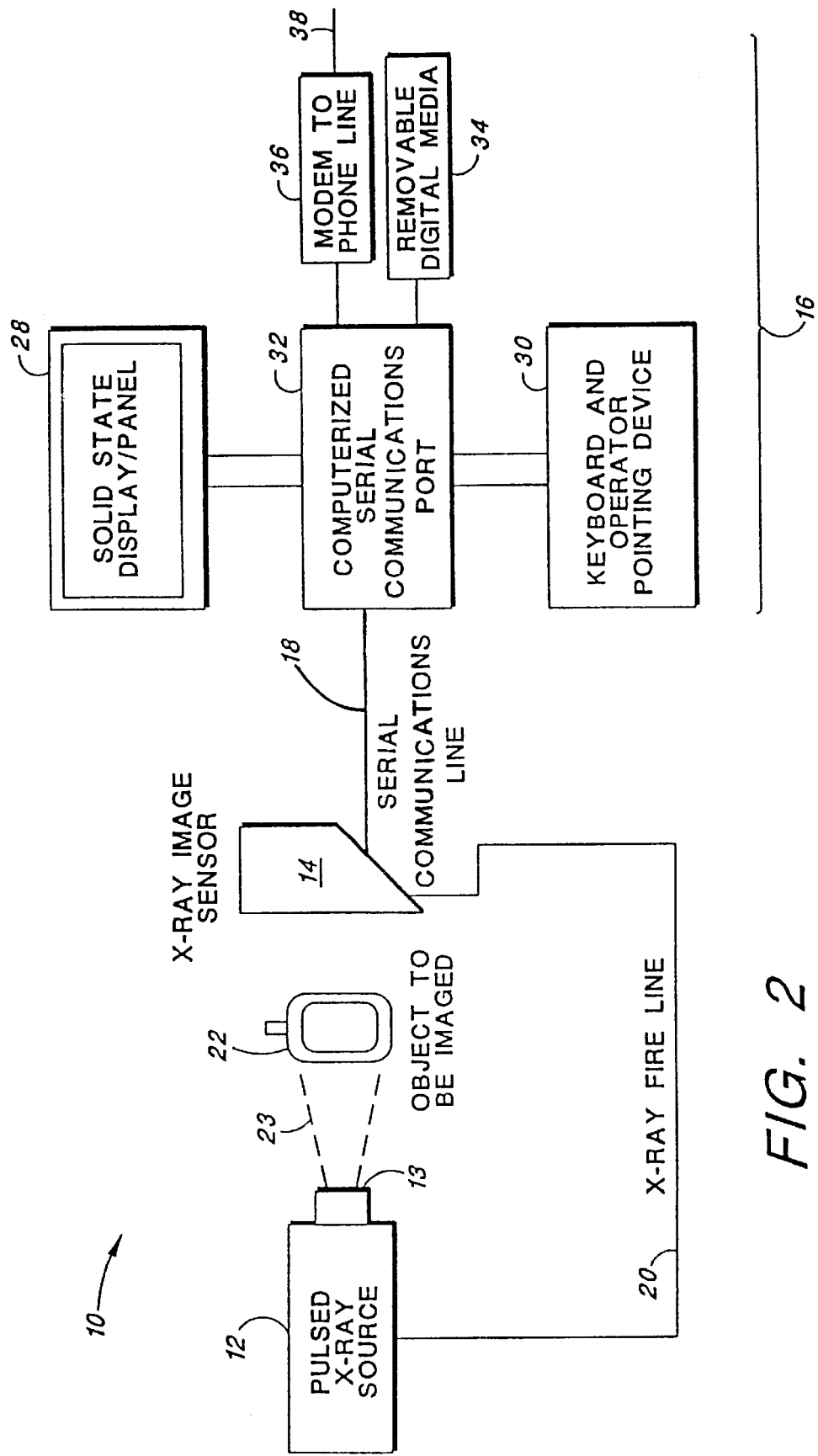
FIG. 2 is a block diagram of the imaging system.

The following description is of the best mode presently contemplated for carrying out the invention. This description is not to be taken in a limiting sense, but is made merely for the purpose of describing the general principles of the invention. The scope of the invention should be determined with reference to the claims.

Turning first to FIG. 1, there is shown an imaging system 10 made in accordance with the present invention. The system 10 includes three main subsystems: (1) a portable X-ray source 12, (2) an imager 14, and (3) a Display/Control Unit 16. The three subsystems are interconnected with two cables. A first cable 18 is a "long" cable and is connected between the Display/Control unit 16 and the imager 14. The long cable may be as long as 300 feet. A second cable 20 is a "short" cable that is connected between the imager 14 and the X-ray source 12. The short cable is typically less than 10 feet in length.

Advantageously, the system 10 is portable, which means it is sufficiently lightweight and non-bulky to enable a single person to hand-carry its three constituent subsystems and associated cables to a field location where an object 22 to be investigated is located. Once on site, the system 10 is designed to: (1) facilitate quick and easy setup around the object 22 to be investigated, (2) provide rapid image acquisition at the field location, and (3) provide image enhancement tools that aid in the evaluation of the acquired image.

In operation, the system 10 is setup by placing imager 14 next to the object 22 to be investigated, e.g., as close as possible to the object. The X-ray source 12 is then placed, e.g., two to three feet from the imager 14, on the opposite side of the object 22. The display/control unit 16 is then connected to the imager by way of the long cable 18 and is placed a safe distance from the object 22. The X-ray source is also connected to the imager 14 by way of the short cable 20. When everything is properly connected, all three subsystems are turned on, and under control of the display/control unit 16, the X-ray source 12 generates a pulsed X-ray beam (represented by the lines 23) that is allowed to pass through the object 22. The pulsed X-rays pass through respective segments of the object 22 with varying degrees of intensity, or energy, as a function of the contents of the object 22, and are captured or sensed at corresponding pixel areas of the imager 14. The intensity or energy of these pulses that pass through the object 22 are accumulated or summed (integrated) over the duration of the pulsed beam (exposure time), which exposure time may include, e.g., a burst of 15–99 pulses.

At the conclusion or termination of the pulsed beam, the imager 14 has acquired an integrated or summed energy for each pixel of the display area, with the combined collection of all such energies for all the pixels comprising an integrated image signal. The integrated image signal is then transferred to the display/control unit where it is appropriately processed and displayed. Such processing includes digitizing the signal to facilitate its subsequent storage, retrieval, enhancement, display and/or transmission.

Advantageously, the system 10 is designed for safety and ease of operation. X-ray safety is assured, e.g., through the use of the pulsed X-ray source 12. Such pulsed source produces extremely short bursts of X-rays capable of penetrating several inches of most materials, yet generates extremely low radiation dose (integrated exposure) levels outside the direct source beam. Safety is further enhanced by two interlock keys, both of which must be in place and in the "ON" position in order for the X-ray source 12 to be activated. A first interlock key 24 is at the display/control unit 16. A second interlock key 26 is at the X-ray source 12. Moreover, a software interlock is provided as part of the operation of the display/control unit 16. Such software interlock generates and displays a warning message on a screen 28 on the display/control unit 16 and then requires the operator to acknowledge such warning message by pressing a key on a keyboard 30 of the display/control unit 16 before the X-ray source can be triggered.

An additional safety feature is provided through the use of the long cable 18 which permits the display/control unit 16 (and hence the operator) to be located a safe distance (the length of the cable 18) from the object 22 being investigated. The cable 18, for example, may be as long as 180 feet, although in the preferred embodiment it is only about 60 feet (typically provided through two 30-foot sections). The cable 18 could be made even longer, if desired, if appropriate line drivers are inserted into the line at regular intervals, and/or if a different transmission medium is used (e.g., fiber optic cable, and or RF wireless transmission).

Turning next to FIG. 2, there is shown another diagram of the imaging system 10 which illustrates, in block diagram form, essentially the same elements as are depicted in FIG. 1. However, FIG. 2 shows further detail of the display/control unit 16 (which hereafter may be referred to as simply the "control unit 16"), and in particular shows that the control unit 16 includes a serial communications port 32, a solid state display panel 28, a keyboard and operator pointing device 30, removable digital media 34, and a modem 36 to allow connection to a phone line 38. The long cable 18 connects between the serial communications port 32 and the imager 14 (sometimes referred to herein as an "X-ray sensor"). The signals sent and received over the long cable 18 include the integrated image signal and a trigger signal, as well as an operating voltage (power) for the imager 14. The trigger signal triggers both the integration circuitry within the imager 14 as well as the X-ray fire line going to the pulsed X-ray source via the short cable 20.

Advantageously, the pulsed X-ray source 12 may be realized using any suitable commercially available X-ray source. One commercially available X-ray source that may be used within the system 10, for example, is the Golden Inspector® Model 200 X-ray source manufactured by Golden Engineering Inc., P.O. Box 175, Centerville, Ind., 47330, the operator's manual for which is incorporated herein by reference. The Inspector Model 200 X-ray source has a maximum output energy of 150 kV, and produces about 3.0 mRem output dose per pulse at one foot (on the beam centerline, with 2.5 mm aluminum filter). It includes a built-in electronic counter to provide from 0–99 pulses. The X-ray pulses that are generated have a nominal pulse width of 50 nanoseconds. The nominal pulse rate is 20–25 pulses per second (pps). It is a modular design having approximate dimensions of 4.2 inches wide by 4.2 inches deep by 15 inches long. It weighs only 20.5 pounds with a battery. It also includes a standard camera tripod mounting plate (¼–20 thread). Besides a battery, it includes a power cord and self-contained 29 volt rechargeable battery pack. The source 12 may be battery operated or it may be plugged into a 110/220 VAC, 50/60 Hz power outlet using conventional power cords. Switching between battery and line power is automatic. Other equivalent portable X-ray sources could, of course, be used in lieu of the Golden Inspector Model 200 X-ray source.

The X-ray source 12 should be positioned so that the beam centerline intercepts the "imager screen" near its center. The imager screen is that portion of the imager 14 designed to be impinged by the pulsed X-rays that pass through the object 22, and hence that portion of the imager 14 which captures the X-ray image. One of the advantages of using the modular X-ray source 12 is that it can be readily adjusted in height and orientation by positioning it on the floor, on risers, or on an adjustable platform, as required. The imager 14 may also be adjusted, as required, so that the region of interest of the object 22 is as close as possible to the imager screen. The location of the imager screen on the imager 14 may be denoted by a rectangular indentation on the face of the imager 14, or by other suitable markings (e.g., painted lines). The X-ray source is preferably positioned approximately two to three feet from the imager screen for best image results.

It is also preferred that a suitable X-ray source beam filter 13 (FIG. 2) be used with the X-ray source 12 in order to enhance the quality (resolution and contrast) of the resulting image. An X-ray filter typically comprises a thin metal sheet that is placed over the exit aperture of the X-ray source to remove by absorption and scatter a fraction of the low energy X-rays. It has been found that, depending on the thickness and material composition of the object imaged, very low energy X-rays in the source beam may not be contributing to the formation of the X-ray image formed (which X-ray image is, in essence, an X-ray "shadow" of the object(s) placed in the path of the X-ray beam) by transmission through the object. These low energy X-rays, however, are believed, in some instances, to decrease the quality of the image by contributing to statistical noise, thereby resulting in a decrease in image resolution and contrast through scattering. Hence, the filter 13 is used to remove such low energy X-rays. The type and thickness of the filter 13 to be used typically depends on the thickness and composition of the object.

When imaging a thin, or lightweight target, the filter 13 should be of minimal thickness, such as 0.005 to 0.010 inch thick copper or 0.020 to 0.030 inch thick aluminum. If the target 22 contains dense materials, a more substantial filter 13 may give better results. A copper filter of 0.020 inch thickness may help image effectively steel objects. Alternatively, use of a 0.050 inch thick aluminum filter is also believed to produce satisfactory results.

The problem of imager saturation, sometimes referred to as "blooming", can be corrected by decreasing the exposure time. It has also been learned that imager saturation can be lessened using a suitable beam filter 13. When trying to image objects which have adjacent areas of high and low density materials, saturation of the less dense regions can hide detail in the dense areas. By employing the different thicknesses of filtering materials, it has been found possible to reduce or even eliminate this "blooming" problem, reduce noise due to scattering, and produce a more detailed radioscopic image.

The imager 14 is realized by application of a suitable X-ray sensor. One type of X-ray sensor that may be used for the imager 14, for example, is an integrating CCD camera subsystem 14' modified in accordance with the present invention, as shown in FIG. 3. As seen in FIG. 3, the CCD subsystem 14' includes a lightweight metal housing 40, e.g., made from 0.06 inch thick aluminum, that holds an X-ray light converter screen 42, which screen 42 functions as the "imager screen" referred to above. Typically, the screen 42 is eight by ten inches in size, and is realized using a suitable scintillating screen, e.g., a phosphorus scintillating screen. As the X-rays strike a particular pixel area of the scintillating screen 42, flashes of phosphorescence occur having an intensity or energy proportional to the energy of the X-ray beam. Such flashes are then optically guided through a suitable optical path, which includes a front surface mirror 44, through a fast lens 46, to a solid-state, compact, integrating charge-coupled device (CCD) camera 48.

The image is recorded within the CCD camera 48, and is converted to a serial communications stream that is sent to the control unit 16 via the long cable 18 (FIGS. 1 and 2). The housing 40, in the preferred embodiment of the imager 14', includes a built-in handle to help transport it. Such handle may also be positioned to help hold or support the housing so that the screen may be maintained in a generally vertical position when the imager 14' is oriented as shown in FIG. 3.

A preferred imager 14' has approximate dimensions of 10.3 inches wide by 12 inches high and 7 inches deep. The weight of the imager 14' is under 10 pounds. Operating power for the imager 14' is obtained through the cable 18 from the control unit 16, and is typically provided by way of a power supply voltage of 12 volts. Hence, like the other components of the overall system 10, the imager 14' is readily portable and easy to use at an on-site field location.

As indicated previously, the CCD camera 48 integrates the image over a prescribed number of X-ray pulses (exposure time). Advantageously, the integration of the light image (resulting from the flashes of phosphorescence that occur as the X-ray pulses impinge the scintillating screen) occurs on the CCD chip, as opposed to being carried out using off-chip electronic circuitry. The normal charge readout is inhibited during the integration period, thereby making such charge readout available at the completion of the integration period for use as the standard video signal, or integrated signal, previously referenced. Further, integration only occurs in synchrony with the generation of the burst of X-ray pulses, thereby effectively blocking out "noise" that is present at times other than when the X-ray burst is present.

In the preferred embodiment of the imager 14', the CCD camera 48 is realized using an 6600 Series Board Level Monochrome CCD Camera obtained from COHU, Inc. 5755 Kearny Villa Rd., San Diego, Calif., 92123. The 1100 Series CCD cameras feature a ½ inch-format on-chip microlens sensor, mounted to an electronic board whereon supporting electronic circuitry is placed, such as driver circuits, video generation circuits, power supplies, and the like. Advantageously, the 6600 Series cameras may readily be configured for custom purposes. In this instance, these modifications include a redesign of the system to a single circuit board with a single digital channel having TTL drivers compatible with the Digital Video Transmission (DVT) circuit also enclosed in the imager housing. The camera additionally is modified to digitally switch gain as well as change clock frequency and bandwidth to optimize signal to noise performance. The camera also has a provision for external control of its integration period from a signal generated on the DVT board. All of these functions can be selected on the remote computer display console and are transmitted back to the camera via the imbedded processor contained on the DVT board.

With a Series 6600 CCD camera (or equivalent camera where a microlens sensor is mounted on an electronic board), it has been found that the CCD camera 48 needs to be protected from exposure to ionizing radiation damage. Two types of problems may arise. First, X-rays which penetrate the imager 14' without interacting with the scintillating screen 42 may strike the CCD chip of the camera 48. If this happens, visible specks of white light appear on the image, thus reducing the image quality. Second, prolonged exposure to such radiation can prove to be harmful to the integrated circuit components, e.g., the CCD chip or other integrated circuits used to generate the video signal, possibly resulting in failure of such circuits.

In order to reduce the number of X-rays that strike the camera 48, the camera 48 is encased in a 0.125 inch thick lead housing or shield 50. The preferred shield 50, for use with the particular CCD camera 48 specified above, is shown in its folded state in FIG. 5, before placing it around the CCD camera 48. In addition, a 0.25 inch thick lead plate 52 may be placed between the CCD-chip and incident X-ray radiation in order to further shield the CCD chip from stray X-rays.

A further aspect of the invention concerns the use of the first surface of the mirror 44 (FIG. 3) to direct the image of the scintillating screen 42 to the CCD camera 48. Employing the mirror 44 as shown, i.e., in line with the X-rays that strike the scintillating screen, permits placement of the CCD camera 48 at a location outside of the main X-ray path, thereby significantly reducing the number of X-rays that might otherwise directly strike the CCD camera or its associated electronic components. (Note, any the X-rays that pass through the scintillating screen 42 would also pass through the mirror 44.)

As indicated, the preferred CCD camera 48 is an 1100 Series CCD camera made by Cohu of San Diego, Calif. Representative specifications of the Cohu's 1100 Series camera are as follows:

| | |
|---|---|
| Pick Up Device: | ½" Interline transfer, microlens sensor |
| Active Picture Elements: | 659 (H) × 494 (V) |
| Pixel Cell Size: | 9.9 $\mu$m (H) × 9.9 $\mu$m (V) |
| Total Pixel Elements: | 692 (H) × 504 (V) |
| Resolution: | RS-170: 580 horizontal TVL, $\geq$350 vertical TVL |
| Synchronization | Horizontal and vertical derived from selectable crystal oscillator (24.545 and 6.134 MHz) |
| Shutter | 1/60 to 1/10000 |
| Power | 12 VDC, 3.6 W max |
| Size | 1.75 × 3.88 × 1.00 inches |

Another type of X-ray sensor that may be used as the imager 14 is a flat panel sensor 14", as shown in FIG. 6. Such sensor 14" offers the advantage of being flat and relatively thin so that it can be positioned into tight spots, and further eliminates the need for a mirror(s) and/or lenses to define an optical path. The sensor 14" includes a conventional X-ray scintillation screen 42' that is in direct contact with a flat panel, amorphous silicon, TFT (thin film transistor) photo sensor 52. The TFT photo sensor 52 is made on a glass or ceramic substrate 54, and includes a matrix of thin film transistors 60. Each TFT further has its own thin film sample and hold (S&H) photodiode 62 associated therewith. The matrix of TFT's and S&H diodes is sufficiently dense so that each TFT 60 and associated S&H photodiode 62 corresponds to a different pixel of the sensor 14". The S&H photodiode 62 senses and accumulates all of the light flashes produced at the corresponding pixel of the scintillation screen 42' during the integration time. At the end of the integration time, the accumulated signal at each pixel site that is held by the corresponding S&H photodiode 62 is read through its corresponding TFT transistor 60 through appropriate row drive electronics 56 and column drive electronics 58, in conventional manner. Such accumulated signals, for all of the pixels of the sensor 14", thus comprise the integrated image signal for a given exposure time.

Further details of the manner of making and using a flat panel sensor of the type illustrated in FIG. 6 as the sensor 14" are described, e.g., in Street, et al., "Amorphous Silicon Arrays Develop a Medical Image," *IEEE Circuits and Devices*, pp. 38–42 (July 1993); and Wu et al., "Imaging With Page-Sized A—Si:H 2-Dimensional Sensor Arrays,"

*SPIE Proceedings*, Vol 2172 pp. 144–154. Both of these references are incorporated herein by reference.

Figure 4:
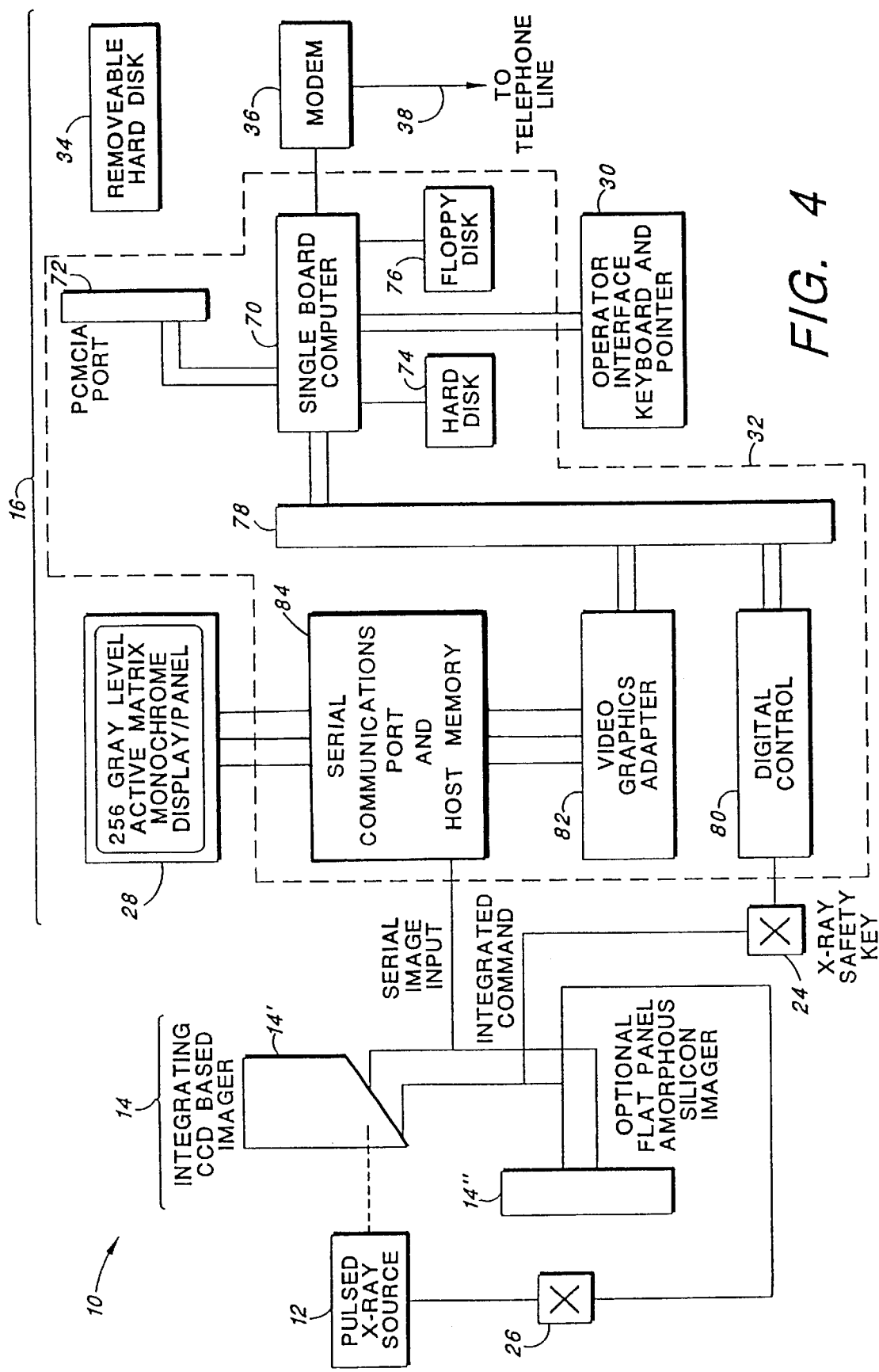
FIG. 4 is a block diagram of the imaging system and shows additional detail of the display/controller unit.

Turning next to FIG. 4, a more detailed block diagram of the imaging system 10, and particularly of the control unit 16, is illustrated. As seen in FIG. 4, at the heart of the control unit 16 is a single board computer (SBC) 70. The SBC 70 is connected in conventional manner to a PCMCIA port 72 (adapted to interface with a removable hard disk 34), a hard disk 74, a floppy disk drive 76, a keyboard/pointer 30, and a modem 36, all of which are of conventional design. The SBC 70 further interfaces, through a suitable bus 78, with digital control circuitry 80 (for generating-/interfacing the digital control signals that are sent to the imager 14 and the X-ray source 12), a video graphics adapter 82 and a serial communications port and host memory 84, all of which may also be of conventional design, except as indicated below.

Advantageously, all of the components of the control unit 16 are effectively those of a conventional personal computer (PC).

While any suitable PC could be used and modified for use with the invention, the preferred PC is at a minimum a 486 class microprocessor, or better, operating at a preferred minimum clock speed of about 33 MHz. The unit 16 has dimensions of only 10.5 inches by 12.5 inches by 5 inches, weighs only about 15 pounds (including a battery pack), and is housed in a "suitcase" housing that, when closed, does not readily identify its function. Such disguised appearance can be an important feature for some applications of the invention so that the unit can be easily carried into a desired field location, e.g., a busy airport terminal, without initially drawing undue attention thereto.

The preferred active matrix flat panel display for use with the control unit 16, but certainly not the only flat panel display that could be used, is a LDH096T-11 display made by Flat Panel Display Co. of Eindhoven, The Netherlands. The LDH096T-11 is a 9.5 inch diagonal LCD module that comprises an Active Matrix Liquid Crystal Display, an integrated adjustable backlight and module electronics. The module electronics facilitate interfacing with commercially-available VGA chipsets, and can display either 16 or 256 levels of gray depending on user selection. The display resolution of the LDH096T-11 is 640 by 480 dots, with a dot pitch of 300×300 $\mu$m. The contrast ratio is better than 60:1 at optimum viewing angles, and the brightness is 60 cd/m$^2$. The active area of the display is 192 by 144 mm. The power consumption, including backlight, is only about 2.5 Watts (nominal). The supply voltage for the display is 5 volts.

A preferred control unit 16 for use with the present invention comprises a modified SafeCase® Series 4000 Rugged Portable Computer made by Industrial Data Systems, Inc., 14900 Woodham Drive, Building 170, Houston, Tex. 77078-6016. The Series 400 computer is ordered to include a pentium microprocessor with a clock speed of 133 MHz, 8 MB of RAM, a 3.5" high density floppy disk drive, and at least a 210 MB hard drive. The basic unit offered by Industrial Data Systems (IDS) as specified above is further modified for 120/220 VAC 50/60 Hz/12 VDC operation, including a battery charger that charges the battery automatically whenever the unit is connected to a 120/220 VAC power line. To enhance battery operation, a Microbus MAT 752 low power 486DX/33 CPU board is installed in the unit 16 as the SBC 70. with such low power CPU board, a fully charged battery pack permits 75 to 80 minutes of operation of the unit. The charge level of a given battery pack can be tested at any time using a built-in push button and LED display located at the lower right corner of the battery pack. The battery packs may also be charged external to the unit 16 using a suitable battery pack charger.

As additional modifications to the Series 4000 Portable Computer, an Interlink Durapoint mouse pad pointing device, or other pointing apparatus, is built into the top panel the case (or otherwise made available to the user). Preferably, such pointing apparatus is positioned to be centered just below the keyboard so that a user can manipulate it with his/her thumbs while keeping his/her fingers on the keyboard. A PCMCIA Type III connector is also added to the top panel, and the Microbus CPU Board is connected to drive this port. It is through this port that removable storage media, or other peripherals, may be connected to the Microbus CPU Board. In addition, the I/O (input/output) expansion plate of the unit is punched to accept an Amphenol #165-159236 connector and cable, which when installed and connected to the Microbus CPU Board, functions as the connector for the long cable 18. The LCD panel is modified to accept the above-described FPD LDH096T-11 display 28, and the panel driver circuitry 86 (shown in FIG. 6) is appropriately installed within the unit 16 so as to drive the display 28 as controlled by the Microbus CPU board. Also installed in the unit 16 is an internal modem and external RJ-11 jack to facilitate modem communications.

A preferred serial communications port is an industry standard 10/100 Ethernet adaptor.

The Video Graphics Adapter (VGA) 82 of the control unit 16 comprises a standard VGA board, as is used in any personal computer providing VGA graphics.

The digital controller 80 of the control unit 16 functions to provide an appropriate isolated interface between the control unit 16 and the imager 14 and X-ray source 12 relative to the trigger or synchronization signals that must be sent to the imager 14 and X-ray source 12. More particularly, for the preferred X-ray source 12 and imager 14 described above, the controller 80 produces a TTL (transistor-transistor logic) electronic synchronization signal which when driven to a ground potential accomplishes both (1) the firing of the X-ray source 12, and (2) the integration of the image signal at each pixel site within the imager 14. When the TTL signal is returned to +5 VDC, the X-ray source is inhibited, and the integrated signal is read out of the imager 14 after the next video vertical interrupt. The net result (and desired goal) is that the rapid read out of the video signal from the imager 14 is properly synchronized with the digitizer of the image processor via serial communications port and host memory 84.

As seen in FIGS. 1, 2 and 4, the X-ray source 12 is connected to the control unit 16 through the imager 14. That is, the long cable 18 is connected between the control unit 16 and the imager 14, and the short cable 20 is connected between the imager 14 and the X-ray source 12, and there is not direct cable connection between the control unit 16 and the X-ray source 12. An isolation relay is used at the imager 14 to apply a trigger (or "fire") signal to the X-ray source 12 through the short cable 20 as soon as the TTL synchronization signal is pulled low (or no longer than one frame time thereafter, where one frame time is, e.g., the vertical blank interrupt period, typically ⅟₆₀ of a second). The X-ray source continues generating its burst of X-ray pulses until the TTL signal goes high (or until no longer than one frame time after the TTL returns to +5 VDC). Advantageously, use of the isolation relay keeps electrical noise from getting into the video signal or affecting the stored image on the CCD chip. Thus, it is seen that the imager 14 is enabled (its "shutter"

is open to receive an image) at the same time as, or perhaps even just slightly before, the X-ray source 12 provides its burst of X-ray-pulses, and remains enabled for so long as, or perhaps even just slightly longer than, the burst of X-ray pulses ends. After completion of the exposure, i.e., within one frame time thereafter, the integrated signal acquired at the imager 14 is downloaded to the image processor via serial communications port and host memory 84, and is thereafter available for display at the active matrix display 28 and/or for storage within any of the available storage media used by the control unit 16.

Advantageously, because the control unit 16 is based on a PC-type digital computer, and because of the conventional components used within such computer, both in terms of hardware and software, it is capable of accomplishing a wide variety of image acquisition, manipulation and data storage tasks. Many of these tasks may take advantage of recent advances in Graphical User Interface (GUI) technology, particularly in view of the fact that the familiar MICROSOFT (MS) Windows operating system is being used. For example, with hardware which supports "Digital Chromoakeying", it is possible to superimpose images stored in the memory of the image acquisition memory buffer with the MS Windows desktop display. Such capability provides a very compact and convenient user interface.

Further, because PC-based technology is used within the control unit 16, there exists great flexibility in how the resulting data is stored and transmitted. For example, the conventional TIF binary file format, commonly used for faxes, drawings, and other graphical (digitized) displays/images in the PC-based environment, may be used to store and manage the digitized images. Fortunately, a significant body of commercially-available software exists to aid in the handling, storage, and management of such displays. In addition, such TIF images can be copied to a standard 1.44 MB floppy diskette, using the floppy disk drive included as part of the control unit 16, or to a standard removable hard drive (which has the capacity to store hundreds of such images) using the PCMCIA port, or transmitted via the modem 36. As a result, the images can be transported, transferred and/or copied onto any other PC compatible system. Such images can then be viewed, manipulated, and/or printed using one of the numerous graphics and desktop imaging programs which are commercially available.

The control unit 16 stores the digital image in a host buffer memory (FIG. 4). Such storage of the image allows the host computer, i.e., the SBC 70, to perform mathematical calculations, on a pixel-by-pixel basis, in order to enhance and emphasize particular details in the X-ray image.

Among the types of mathematical calculations that may be performed on a pixel-by-pixel basis are various convolution techniques, accessible through commercially-available software, that modify the displayed image to produce a variety of effects. These effects include: (1) fine sharpening, which subtly increases the clarity of an image by enhancing high frequency components, making edges of objects appear sharper; (2) coarse sharpening, which is a variation of fine sharpening, but which produces a more dramatic noticeable sharpening; (3) smoothing, which reduces the "grainy" appearance of an image having excessive high frequency noise; (4) horizontal edge detection, which suppresses (i.e., turns black) all pixels in an image except for those which form horizontal edges of objects in the image, thereby causing such horizontal edges to appear white, and making them stand out in high relief; and (5) vertical edge detection, which does the same thing to vertical edges that the horizontal edge detect does to horizontal edges.

It is noted that other mathematical operations and functions could also be used in addition to, or in lieu of, the above listed convolution techniques in order to sharpen and enhance a given image. For example, multiple image arithmetic calculation functions, (i.e., pixel-to-pixel Addition, Subtraction, Multiplication, Division, And, Or, Xor, etc.), Blob Analysis, Pattern Analysis, Fast Fourier Transforms, and other more extensive convolution techniques, could be performed.

Moreover, in addition to mathematical manipulation, the control unit 16 permits a wide variety of display flexibility, which also enhances the desired details of an acquired image. For example, zooming by factors of 2 and 4 are supported, allowing small details to be magnified and viewed in greater detail. Panning and scrolling functions are also available in conjunction with the zoom capability to allow a user to move about within the magnified image. A contrast stretch function, discussed in more detail below, is further provided which interactively allows the user to change the displayed contrast and brightness of specific grayscale regions of the image. Such contrast stretch function is particularly useful for increasing the brightness and clarity of very dense objects.

An invert function is likewise provided within the control unit 167 which changes the image from a black-to-white "positive" image into a white-to-black "negative" image. Such function aids radiographers who are more comfortable viewing images as they would appear, e.g., on X-ray film.

As indicated, the control unit 16 preferably operates in a *Windows*-based mode, thereby providing an operator of the system, once the system has been set up and turned on, the ability to select various options related to the imaging task at hand. Such options are controlled by appropriate applications software that is stored on the unit's internal hard drive.

Figure 7:
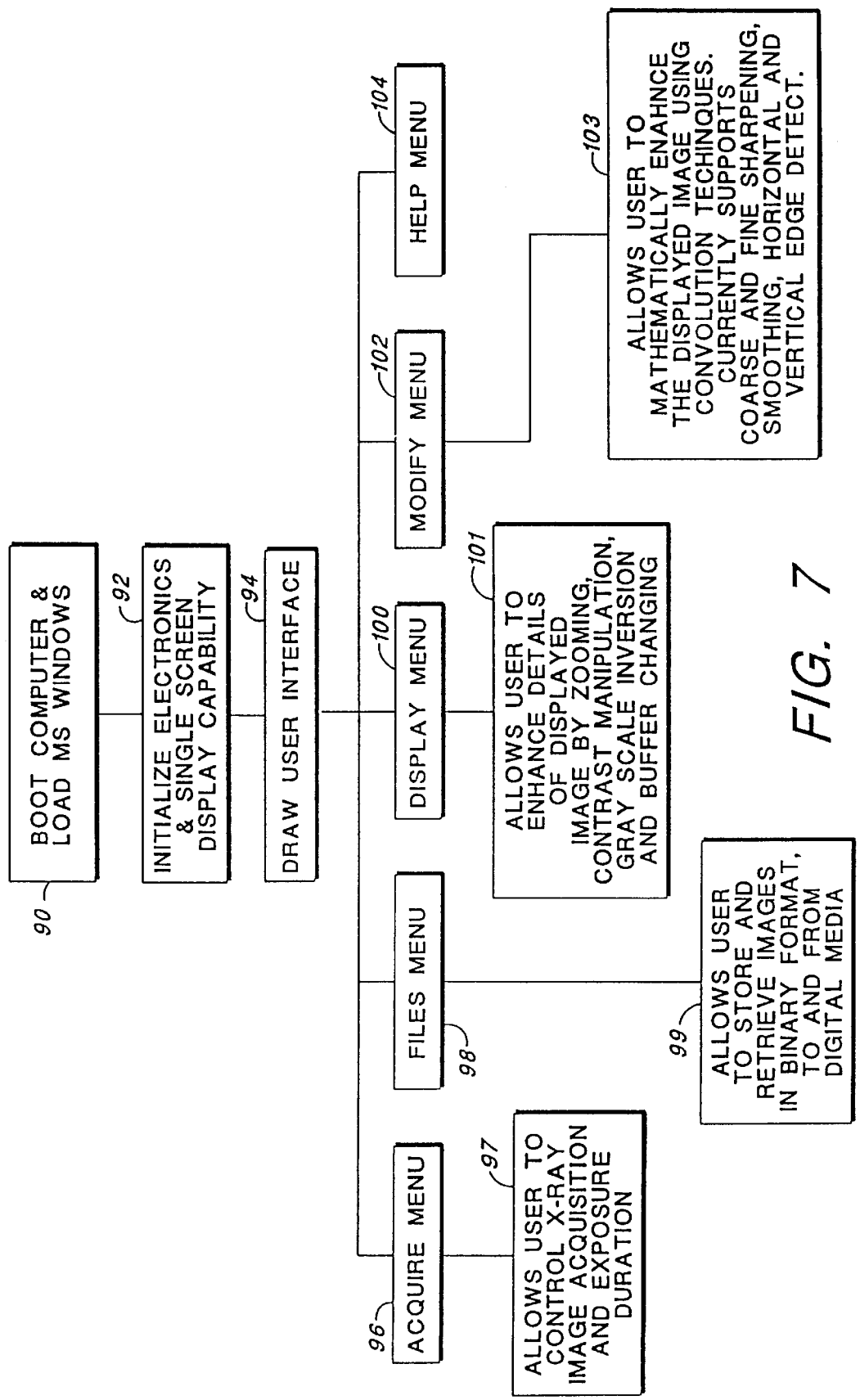
FIG. 7 depicts the various software modules that may be invoked by a user of the imaging system of FIGS. 1 and 2.

A flow diagram of the software control used within the unit 16 is illustrated in FIG. 7. As seen in FIG. 7, when power is first applied to the unit, the computer is booted on and *Microsoft Windows* is loaded (block 90, FIG. 7). The electronics of the image processor via serial communications port and host memory 84 are then initialized, power-on diagnostics are performed, and the single screen display capability is verified (block 92). Once initialized, a User Interface Main Menu is drawn on the screen (block 94) using a conventional windows format.

The User Interface Main Menu screen allows the user to select one of five options. A first option (block 96, FIG. 7) allows the user to get ready to acquire an image. Such option (as indicated at block 97) provides the user with an acquire menu that allows the user to control the X-ray image acquisition and exposure duration. Further details associated with the selection of the "Acquire" option are presented below.

A second option (block 98) provides the user with a "files" menu. The files menu allows the user to store and retrieve images in binary format to and from digital media (block 99), e.g., an internal hard drive, a floppy disk, or a removable hard drive.

A third option (block 100) provides the user with a "display" menu. The display menu allows the user to enhance details of the displayed image (block 101) by, e.g., zooming, contrast manipulation, grayscale inversion, and buffer changing.

A forth option (block 102) provides the user with a "modify" menu. The modify menu allows the user to mathematically enhance the displayed image (block 103) using convolution techniques. Such mathematical enhancements include, at the present time, coarse and fine sharpening, smoothing, and marking horizontal and vertical edge detection.

A fifth option (block 104) provides the user with a "help" menu. The "help" menu provides the user with whatever information may be helpful to the user, e.g., a further description of the other options, the latest enhancements that have been included in the software, and/or any other information that helps the user debug any problems he/she may be experiencing with the operation of the system 10.

Figure 8A:
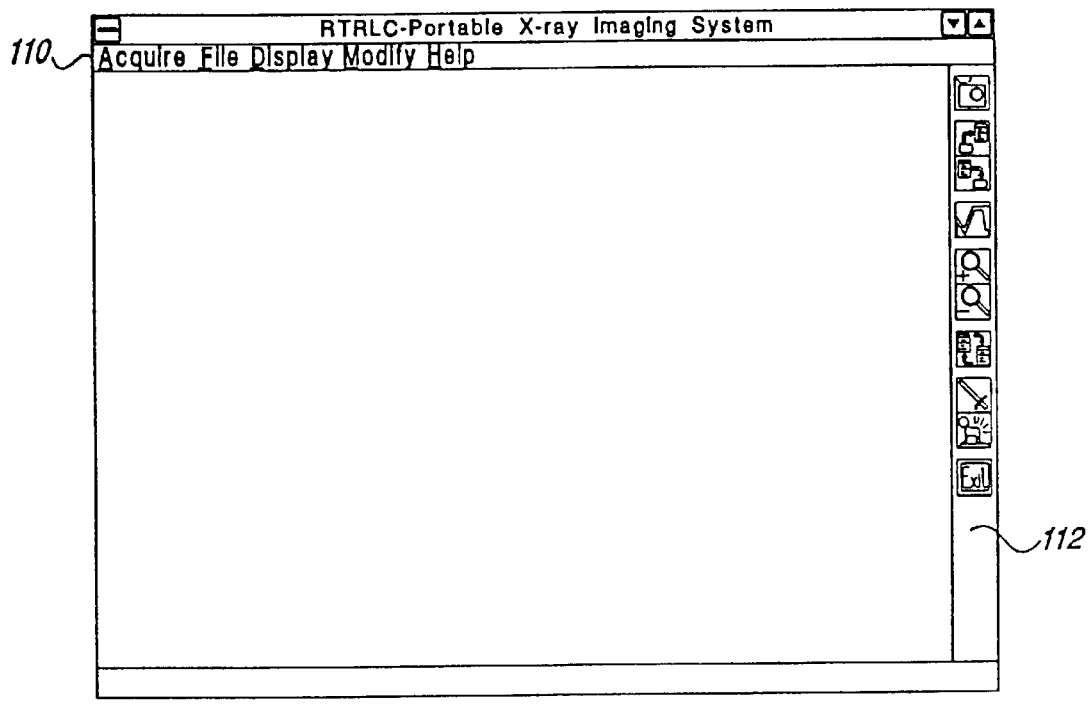
FIGS. 8A, 8B and 8C respectively depict various embodiments of windows or "screens" that are displayed to a user as different control options are selected.

A representation of the User Interface Main Menu is presented in FIG. 8A. This menu is displayed on the display screen 28. Note that the Main Menu appears as a conventional "window" for use within a *Microsoft* windows environment. There is a menu bar 110 located across the top of the screen, and a column of icons 112 located on the right of the screen. From this main *Windows* menu, the user can access the various options provided by pull-down menus or icons associated with each option. The functions which can be activated by the icons are a subset of the functions which can be accessed through the pull-down menus.

As with any *Windows* environment, selection and activation and/or initialization of each of the various activities represented by the corresponding icons or pull-down menu options is made using the arrow cursor displayed on the flat panel display, or by using keyboard selections consistent with the standard *Windows* applications. That is, a function represented by an icon is activated, e.g., by simply moving the arrow cursor to the point within the appropriate icon using the mouse (or other pointer device) and pressing (or "clicking") the left button on the mouse, or moving the arrow cursor to the named menu item on the menu bar and pressing the left mouse button. Alternatively, the "Alt" key may be pressed simultaneously with the first (or underlined) letter of the named menu item on the menu bar.

Figure 8B:
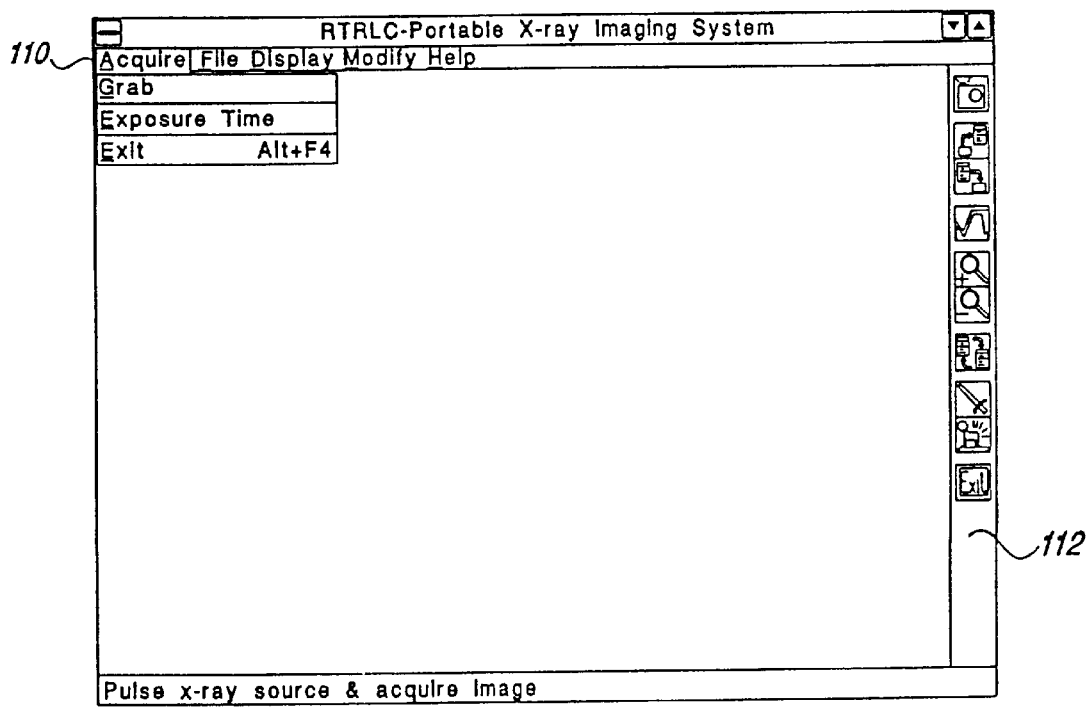

To illustrate, an X-ray image is acquired by moving the arrow cursor and pointing-and-clicking on the Acquire option on the menu bar 110, or equivalent icon in the icon column 112. Such action causes the Acquire pull-down menu to be activated, as represented in FIG. 8B. The Acquire pull-down menu lists three options, as shown in FIG. 8B, including "Grab", "Exposure Time", and "Exit". An image acquisition is referred to as a "grab" because it entails pulsing the X-ray source 12 and "grabbing" the video data resulting therefrom which make up the radioscopic image.

Figure 8C:
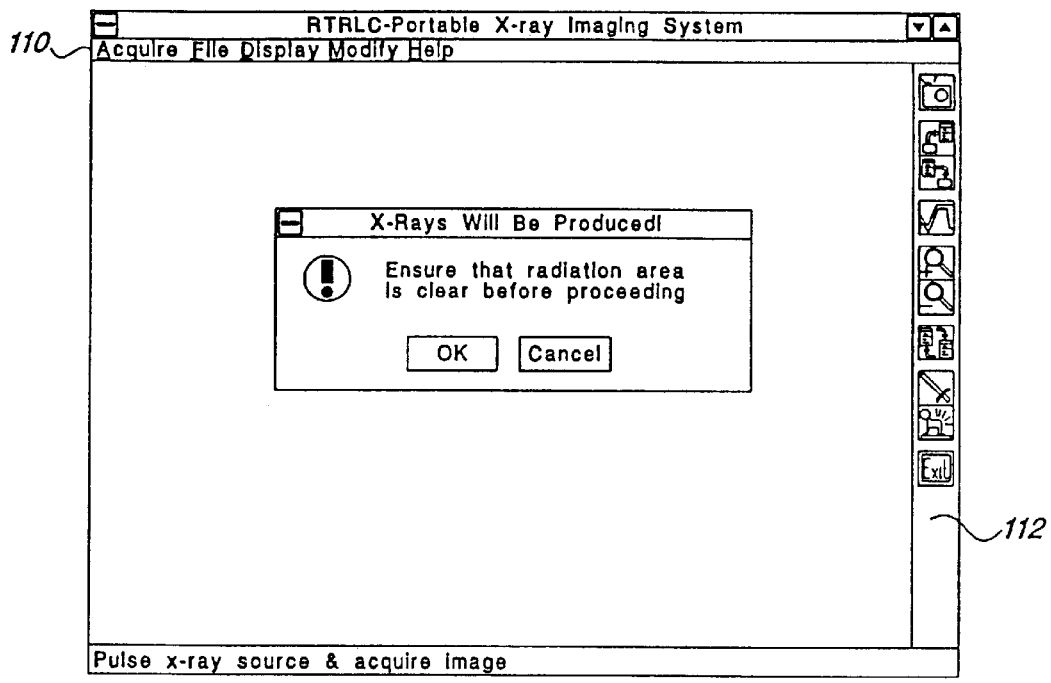

Once the Grab option has been activated, a dialog box appears in the center of the Display Panel as shown in FIG. 8C. This dialog box serves as a safety feature, or software interlock, that warns the operator that X-ray production will be initiated by the next step, and that the X-ray beam area should be clear of all personnel.

As seen in FIG. 8C, two options are provided below the warning: (1) to produce X-rays and acquire an image, the user must use the mouse to point-and-click on the OK button; or (2) the grab request can be cancelled by using the mouse to point-and-click on the Cancel button, which returns the user to the Acquire pull-down menu (FIG. 8B). When the user selects the OK option, the X-ray source pulses immediately and an image forms on the display panel 28. This image is the radioscopic image that is created by having X-rays directed at and pass through the object 22, as sensed by the imager 14, and processed by the circuitry within the control unit 16. Advantageously, at the completion of the Grab sequence, the system returns to the Acquire pull-down menu, and the acquired radioscopic image is displayed beneath the menu overlay graphics.

As mentioned previously, there is an interlock key 24 located on the control panel of the control unit 16, and another interlock key 26 located on the X-ray source. These interlock keys are intended to enhance radiation safety. Both of these keys must be in place and turned to the ON position in order for X-ray production to occur. If either of these keys is not in place and in the ON position, the X-ray source will not fire, a call to the Grab function will time-out, and the system will return to the Acquire pull-down menu without creating a radioscopic image.

Once an image has been acquired, the user may select other menu bar or icon bar options depending on what is to be done next. If the acquired image is not quite right, e.g., due to under or over exposure, or the feature(s) of interest in the image are not properly oriented for definitive evaluation, another image may be acquired after appropriate adjustments are made to the image acquisition time. Such adjustments are made using the Exposure option in the Acquisition pull-down menu, or by adjusting the X-ray source/target/imager geometry. If the quality of the image just acquired is satisfactory, the image can be stored to hard disk or floppy disk using the options found in the File pull-down menu. Further, an acquired image can be visually manipulated using the functions found in the Enhance or Modify pull-down menus. For example, an image which has just been acquired will usually benefit from the Sharp 1 or Sharp 2 enhancements presently offered as the first and second options, respectively, in the Modify menu. These edge sharpening options use the image processor's capabilities to make the acquired image appear sharper than the original image. It is to be emphasized, of course, that the use of such edge sharpening options are meant to be exemplary, not limiting.

One particular image enhancement feature of note is the Contrast Stretch option available through the Display pull-down menu. The Contrast Stretch option of the Display menu is used to change the grayscale level distribution of the displayed radioscopic image to facilitate visualization and evaluation by the operator of features of particular interest. This Contrast Stretch option is a particularly valuable option for the present invention due to the large range of grayscale resolution that is available with the display 28. As indicated previously, the display 28 preferably includes the capability of providing 256 different levels or shades of gray, ranging from black to white, within the displayed image. For example, a pure black pixel is represented by a gray scale of 0, while a pure white pixel is represented by a gray scale of 255.

A mapping function is used to map a given intensity (e.g., number of X-ray pulses received at a given pixel site) to a given grayscale value. Thus, for example, a pixel value of 0 (black) means that no radiation was sensed at the given pixel, whereas a pixel value of 255 (white) indicates that a maximum radiation level was sensed at the pixel site.

In the preferred embodiment, the mapping function that relates the sensed intensity of a given pixel site to a specified grayscale value is linear. It is to be emphasized, however, that the mapping function need not be linear, but can be any value. Performing a Contrast Stretch function changes the "slope" and "offset" of the mapping function. Slope and offset are best understood with reference to FIG. 9.

Figure 9:
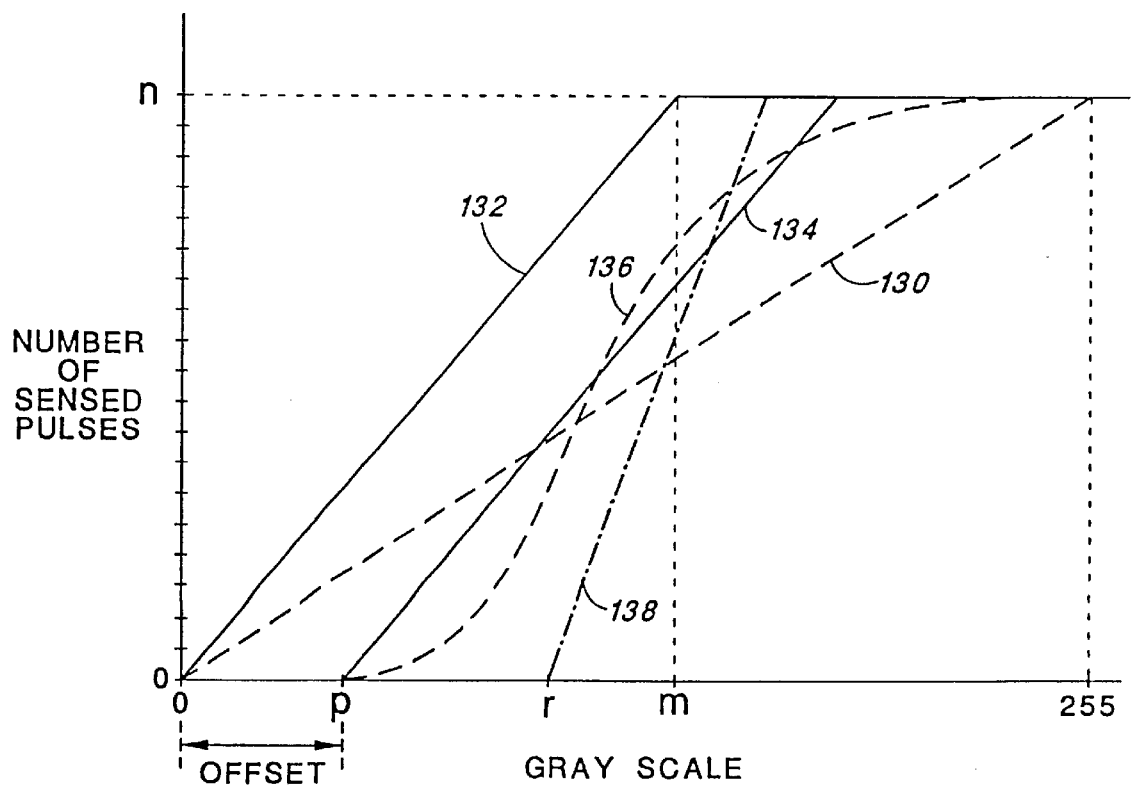
FIG. 9 graphically illustrates the manner in which one of the described embodiments achieves contrast stretching.

FIG. 9 depicts a graph that illustrates representative mapping functions that may be used to map the number of sensed pulses at a given pixel site (vertical axis) to a grayscale value (horizontal axis). Thus, for example, the dashed line 130 represents a linear mapping function with no offset and with a slope of n/255, where n represents a specified maximum number of pulses that can be sensed. The solid line 132 in FIG. 9 represents a mapping function with no offset, and having a slope of n/m where m is about ½ of 255. The slope of line 132 is thus about twice that of the line 130. Solid line 134 has a slope that is about the same as that of line 132, but with an "offset" of p, where p is an integer that is about ⅔ of m. The offset thus defines the location within the pixel value range where the linear (or nonlinear) ramp begins. The dashed line 136, for example, defines a ramp that has the same offset p as the line 134, but is not linear. Rather, the line 136 has a general "S" shape, and thus has a varying slope that is the steepest in the mid range of the number of sensed pulses. The dashed-dotted line 138 has an offset of r and a slope that is the steepest of all the lines shown in FIG. 9.

The present invention thus allows the offset and slope of the displayed image to be readily defined using, e.g., the Contrast Stretch function, and numerous other image enhancement tools, thereby allowing the quality of the displayed image to be improved. In its present configuration, the Contrast Stretch option acts only on the output to the display panel 28. When images are stored to disk and subsequently retrieved, they will not be stretched as displayed prior to archiving. That is, saving an image to hard or floppy disk stores the data in the display memory buffer, but not the video output parameters. Nonetheless, storing and saving the video output parameters, as well as the image, is something that could be done by those of skill in the art if needed and/or desired.

The image enhancement tools used by the present invention are realized using commercially available imaging application development software. Such software may be obtained, e.g., from Matrox Electronic Systems, Ltd., of Quebec, Canada. Matrox provides, e.g., numerous software programs, including a *Windows Utility*, that allows a user to load, grab, create, duplicate, save, transmit, display, overlay, and/or process digital images. All of the enhancement features of the present invention, such as course and fine sharpening, smoothing, horizontal and vertical edge detection, grayscale inversion, contrast stretching, zooming, and buffer changing, are supported by software programs and/or hardware that are commercially available from companies such as Matrox, or other companies like Matrox, e.g., Data Translation, Inc., 100 Locke Drive, Marlboro, Mass. 01752-1192.

As described above, it is thus seen that the present invention provides a high-resolution, solid-state imaging system that utilizes on-chip light integration, thereby eliminating the need for intensifying electro-optic components, and wherein the system is based on a personal-computer controller that facilitates the acquiring, displaying, storing, enhancement, and/or transmitting of a digital image obtained with the system. Advantageously, such system is self-contained, lightweight and portable, and can easily be taken on-site to inspect whatever objects need to be examined without having to move such objects. Once an image is acquired, the image can be immediately sent as digital data over a modem, provided as part of the system, or stored on a floppy disk, or removable hard disk, to facilitate its transfer to an off-site location where the image can be faithfully reproduced for further analysis by off-site experts.

An additional preferred embodiment described as follows, provides a fully digital imaging system in which a pixel-correlated, digital X-ray imager may employ slow scanned pixel interrogation and serial digital transmission for single shot exposure. The improved system 200 for processing radioscopic images of an object under investigation provides improved tracking and digitization, which enhances the on-chip integrated image quality of CCD cameras for use in the portable digital radioscopic system 10. The digital camera 202 described below has the other essential features of integration on-chip for several seconds, which may replace the video based system described above in connection with FIG. 2. The additional embodiment of system 200 includes the use of on-chip integration to build up the signal from the weak source to a level corresponding to a full scale image as well as the ability to use commercial grade CCD devices.

Figure 10:
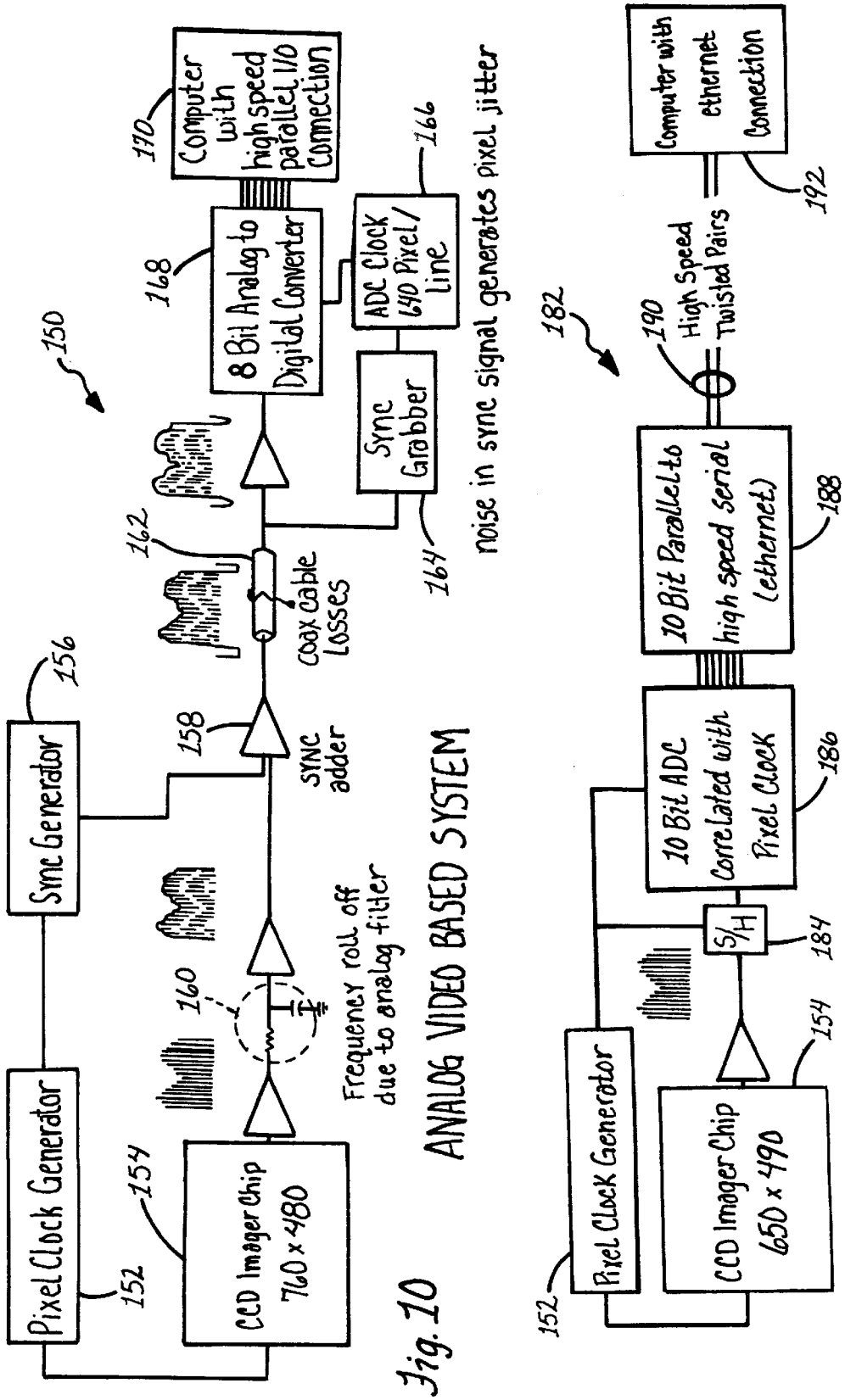
FIG. 10 represents an analog video based system employed in the embodiment of FIG. 2.

FIG. 10 represents an analog video based system as is employed in the embodiment of FIG. 2. Herein, the analog based system 150 uses a clock signal generated by a pixel clock generator 152 for use with a CCD imager chip 154. Additionally, the pixel clock generator 152 drives a sync generator 156, which provides additional and separate clock timing signals for use with a sync adder 158, which is used to create the standard RS-170 video timing and waveforms.

The pixel clock generator 152 thus provides a variable frequency pixel clock for the operation of the CCD imager chip 154 in a mode in which the sampling and digitization of each individual pixel is phase correlated with the clock pulse. Accordingly, the spatial sharpness (i.e., modulation at a given spatial frequency) is enhanced through such correlated sampling of the signal from each individual pixel to produce an image which is only limited by the optical qualities of the CCD 154 itself. Thus, image quality is not affected by the video amplifier, system bandwidth, or any jitter in the timing of a synchronization pulse used to phase lock conventional video digitizers.

Use of digital transmission also eliminates unsharpness caused by the effects of bandwidth roll-off in long cables with analog signals when the digitizer is remotely located from the camera. Accordingly, noise reduction is facilitated for improved contrast sensitivity. As discussed, clock speeds can be slowed to take advantage of lower noise of system amplifiers at reduced bandwidth with no adverse effect on spatial sharpness. Additionally, clock generation and digitizer can be co-located with imager chip to minimize noise pick-up that would occur if the analog voltages were transmitted any significant distance.

Additionally, RC filter 160 is used at the output of the CCD imager chip 154 to filter out spikes in each individual pixel, which tends to degrade the bandwidth of the pixel output from the imager chip 154.

An analog output signal is then provided to the sync adder 158 to form a conventional television waveform by sampling the analog signal out of each pixel, creating a waveform which is a sequence of all of those samples. Subsequently, the analog television signal is then reconverted in the system 150 to provide a digital output. Herein, a sync grabber 164 drives the generated sync signal for use with a 640 pixel per line, analog-to-digital converter clock 166, which drives an analog-to-digital converter (ADC) to provide an 8-bit parallel digital output to a computer 170 having a high speed parallel input/output connection.

It should be appreciated that the generation of the analog signal and the subsequent processing and transmission of the analog signal in system 150 will adversely affect the contrast response over spatial frequency (e.g., television lines).

Use of progressive scan CCD rather than more conventional interlaced device allows exposure to be uniform for all pixels and simplifies readout to digitizer. Many consumer type "interline CCDs can be operated in either interlace or progressive mode and there is significant advantage to the progressive mode which exposes all pixels for the same duration. Additionally, as discussed below, use of a Digital Video Transmission (DVT) Module 204 within the X-ray imager provides the ability to buffer, organize, and packetize the video information into fixed size data packets, serialize and to transmit the digital data from the camera, and to respond to digital controls from the remote operator controller to modify the imager's operation and control the X-ray operation.

Figure 11:
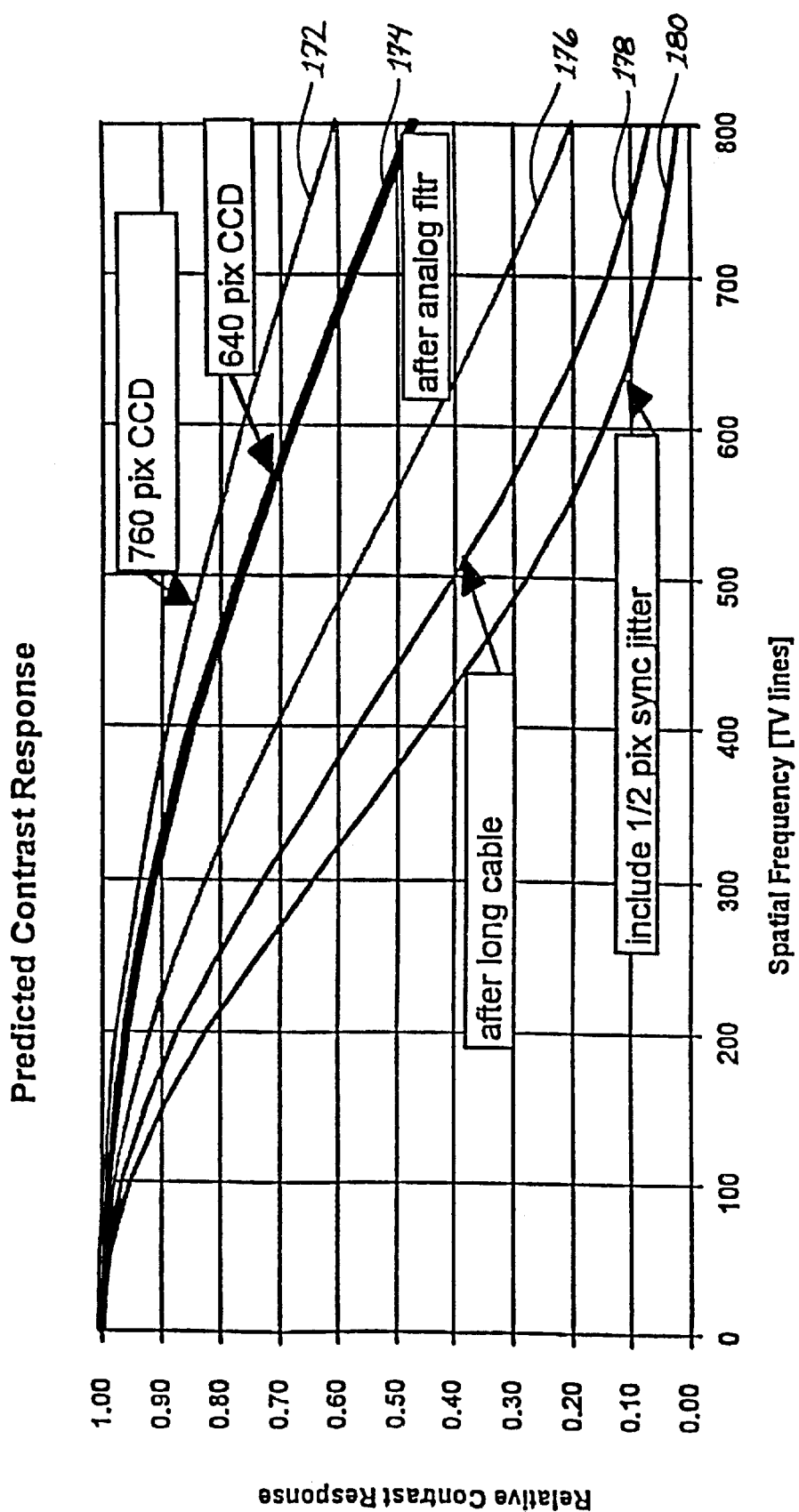
FIG. 11 graphically depicts predicted contrast responses illustrating normalized comparisons with a digital CCD camera and the effects of multiple filters on the video CCD response.

With reference to FIG. 11, the predicted contrast responses between that of a fully digital CCD output, and that of the multiple filter effects on the video CCD signal is graphically illustrated. As will be appreciated, although the CCD imager chip 154 provides a 760×480 pixel matrix, the actual effect of spatial resolution is far reduced by the time the CCD output is filtered, processed as a television signal and then transmitted via coax cable 162 to the remote computer 170. Herein, the computer 170 of FIG. 10 may be the equivalent of the single board computer 70 of FIG. 4 in the embodiment of FIG. 10, described above.

The predicted contrast response illustrated in FIG. 11 shows the 760 pixel resolution from the CCD imager chip 154 at reference numeral 172. Reference numeral 174, on the other hand, shows the resolution of a 640 pixel CCD. After the frequency roll-off due to the analog filtering with the RC filter 160 of the CCD imager chip 154 output, the effective contrast response is reduced significantly as indicated at reference numeral 176, in fact, the resolution is reduced so as to make the effective contrast response from imager chip 154 actually worse than that of a 640 pixel CCD as indicated at reference numeral 174. Additionally, coax cable losses due to a considerable length of cable 162 results in further degradation to the predicted contrast response as indicated at reference numeral 178. The described use of digital transmission techniques, however, facilitates enhanced transmitted X-ray image quality. Finally, noise in the sync signal may generate an additional one-half pixel synchronization jitter, which provides a predicted contrast as indicated by reference numeral 180.

It should be appreciated from FIGS. 10 and 11, generating an analog waveform has a considerable adverse effect upon the predicted contrast response of the resulting image over its spatial frequency. Additionally, the interlace provided with a conventional television signal may provide additional problems. So typically while a video line may start with 760 pixels, i.e., physical pixels initially, passing it down a long cable and putting it into a computer 170 via an 8-bit digitizer, creates a situation in which considerable spatial frequency bandwidth is lost in the process.

FIG. 12 is a block diagram representing a fully digital imaging system 182 in accordance with the present invention. Herein, the pixel clock generator 152 drives the imager chip 154, and the pixel clock also is used to drive a sample and hold 184, and a 10-bit ADC 186 correlated with the pixel clock generator 152. The 10-bit parallel output of the ADC 186 is provided to a 10-bit parallel to high speed serial transmission processor 188 (e.g., ethernet), which provides a serial output for transmission over a high speed serial communication link 190 to a computer 192 having, e.g., an ethernet connection for receiving a serial stream of digital pixels representations. Accordingly, the system 182 processes a digital image by generating the pixel clock, and then acquiring pixels responsive to the pixel clock with a progressive scan of the image to provide a discrete pixel readout of the image by digitizing each pixel on a pixel by pixel basis as the discrete pixel readout is sampled from the imager chip 154. Thus, at computer 192 a signal is received of substantially the same quality as that provided by the CCD imager chip 154 at the front end of the system. This is because each signal from each pixel physically derived from the imager chip 154 is digitized at the camera to create a 10-bit number, which is subsequently transmitted digitally via the communication link 190 to a remote location, rather than transmitting an analog signal to the remote location for digital processing.

As discussed above, use of standard communications protocols are used between DVT module and remote operator controller and display. The return link on the serial communications line is also used to communicate with the embedded controller to modify the pixel clock rate or to vary the imager sensitivity to accommodate a wider range of material thickness that must be penetrated. Communication between the transmission module and the remote operator control is via a commercial serial protocol such as ethernet or fiber-channel. The primary advantage of using a protocol such as TCPIP and ethernet is that there is a built in method of validating each packet of data and the system is compatible with virtually any computer controlled display system with an ethernet connection. Both 10 base T and 100 base T formats are supported by the current design. Advantageously, the described bidirectional communications facilitates the implementation of Digital Wireless operation. By using standard Local Area Networking (LAN) protocols, one can take advantage of the many products designed to support wireless networking of computers. By adding unique user codes and device addresses to the system, one can be sure that only the desired imager and X-ray are addressed by the remote display-controller.

Thus, the system 183 is virtually lossless with respect to the visual response of the CCD imager chip 154 by keeping the inherent modulation response of the CCD itself, which remains high by taking advantage of the correlated pixel sampling to produce the true contrast in the image, as a serialized string of digital pixel data transmissions.

In FIG. 12 the digitizer is thus collocated with the chip in the camera enclosure and the CCD is clocked on a pixel by pixel manner with the signal from each independent pixel being sampled and digitized in a fixed phase with the pixel clock. Because of the coherence of the clocking and digitization, no additional analog filtration is used to smooth out the waveform and hence the full modulation of each pixel is retained. This allows one to use a CCD with fewer (but larger) pixels on each line. The number of pixels per line is exactly the same as the digitized and stored image. The actual spatial response of the system is improved, over the analog system of FIG. 10 having a larger number of pixels per line followed by the analog filter to produce a smooth video waveform.

Additionally, in FIG. 12, fewer pixels are used to cover a single line which makes them larger and hence more sensitive, further improving the signal from the pixel correlated digital system. Because the system 182 no longer needs to support the standard 30 Hz, interlaced, RS-170 format, one can slow the clock of the CCD down significantly which further improves the noise of the readout system. This permits the simplification of data transmission over a twisted pair signal line since only digital data need be sent. The improved digital camera system uses a standard serial protocol such as 100 base T Ethernet of IEEE 1394 serial transmission standards. The slow scanned CCD is used as an analog storage system to eliminate the need for a separate digital storage register. Data from the CCD is clocked out in a progressive scanned pattern (not interlaced) and digitized and the resulting 10–12 bits of data are sequentially transmitted over the serial transmission line to a matching receiver in the computer display unit.

The major advantages of this system are expanded sensitivity and lower noise. The virtually loss less data transfer of the resulting data regardless the length of cable required in a field situation. This system also makes digital wireless RF transmission, as discussed above, with the same advantages in sensitivity, contrast and modulation found in the wire linked digital version.

Because the system is totally digital, its organization is totally independent of the pixel count in either direction. To allow the computer display to know which camera it is looking at, the system supports bi-directional serial data transmission. The intermediate transmission board 188 that converts the parallel digital output from the CCD to the serial format, also receives queries on what its pixel size is, as well as instructions to remotely turn on the X-ray source, integrate the X-ray beam on the CCD, modify the system gain (sensitivity) or otherwise change the data collection mode. The on-board microprocessor controls the function in both directions as well as mediating the transmittal of data and correcting for any errors in the signal.

Figure 13:
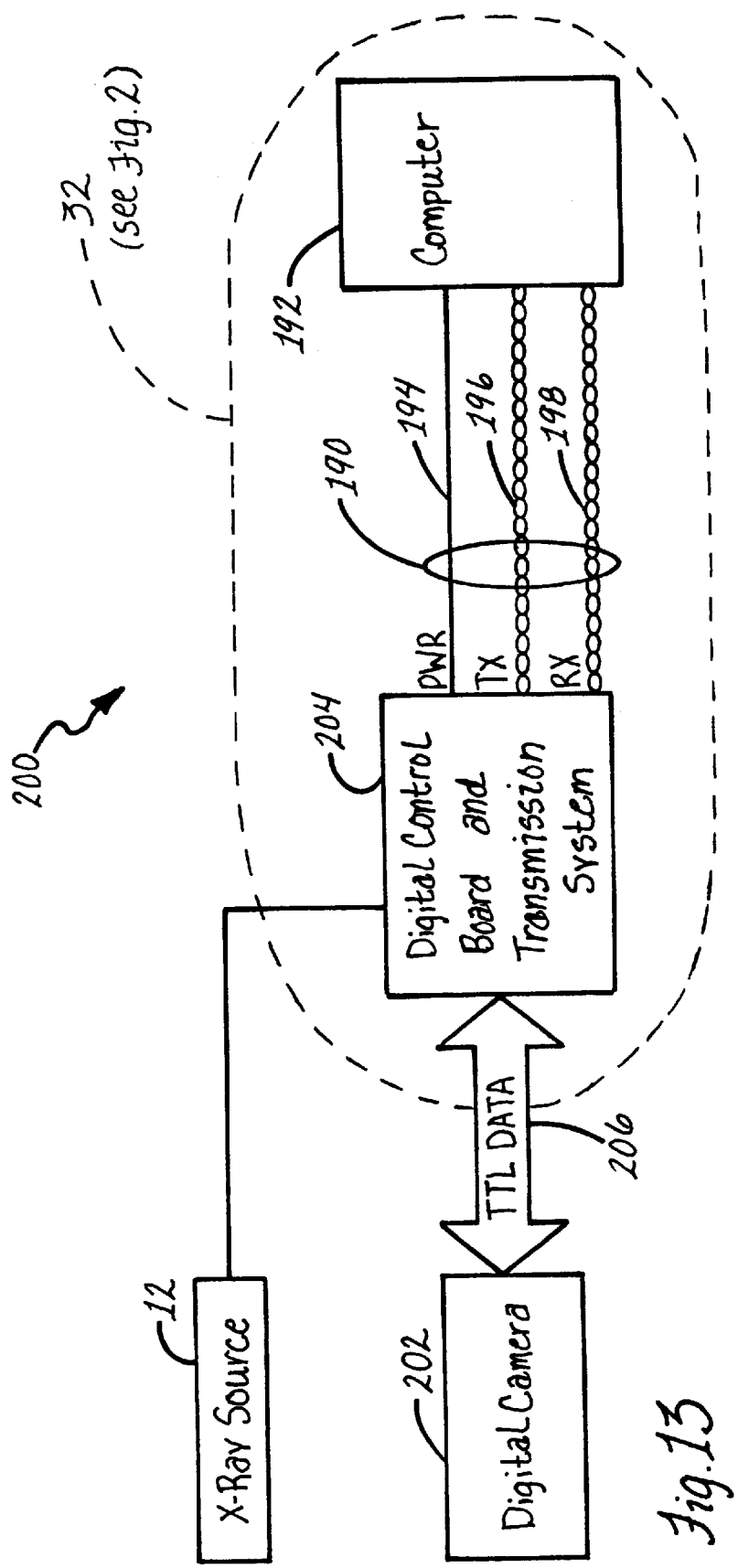
FIG. 13 is a block diagram of a pixel-correlated digital imaging system for processing the radioscopic image of an object under investigation representing the digital imaging system embodiment of the invention.

FIG. 13 is a block diagram of a pixel-correlated digital imaging system 200 for processing the radioscopic image of the object under investigation. Herein, a digital camera 202 communicates with a digital control board/transmission system 204 via a TTL parallel data bus 206 from the digital camera 202. The transmission system 204 provides the 10-bit parallel to high-speed serial function, as that provided by the transmission board 188 discussed above. The communications link 190, as shown in FIG. 13 includes power 194, transmit 196 and receive 198, sending and receiving paths being provided as twisted pairs, which allows for a lightweight cabling such as that provided with a telephone line.

The digital video transmission module 204 provides temporary storage of the digital data in a FIFO field memory that buffers the digital stream from the camera. This buffer allows for the embedded computer to acquire and process the digital data before sending it on to the operator's display system. The DVT module 204 also takes the continuous stream of data from the camera and organizes it into smaller transmission packets that are sent over the serial communications link. The communications link is a high-speed serial line with bidirectional communications. This bidirectional quality allows the embedded controller to validate correct transmission of each packet before issuing a new packet. Additionally, it uses the incoming communications to cause the DVT module to initiate the X-ray exposure and control its duration.

The system 200 conceptually illustrates the serial communications port 32 indicated in dashed lines, which may correspond to the serial communications port 32 described above in connection with FIG. 2. FIG. 13, on the other hand, illustrates that the digitizing and image processing function of the presently described embodiment breaks up the functions between the digital control board/transmission system 204 and the computer 192, which may be located remotely using digital data transmission without the signal degradation and losses associated with analog transmissions. To this end, it should be further appreciated that the communications link 190 may be provided as a computer network such that an image processor may receive the digitized pixels via the computer 192, which now may be provided as a network server. Additionally, the digital camera 202 and transmission system 204 in combination may provide a network or ethernet camera for connection to the communications link 190.

As described below, the revealed camera implementation of the digital camera 202 shown in FIG. 14 includes four basic functional subsections operated by a single master clock generator. These include the CCD imaging chip, the sample and hold and analog to digital converter (ADC), an optional parallel to serial converter and driver to simplify the cabling of the instrument, as well as an optional cooler for the chip to reduce dark current for extended integration periods. Since virtually any type of CCD can be used in this approach, one is not bound to use full frame type devices which require additional shuttering if the source duration is not controlled. One can use a standard interline CCD operated in progressive scan mode which is generally less expensive to implement. CCDs of differing pixel dimensions can be used in different cameras by properly programming the on-board clock generator.

Figure 14:
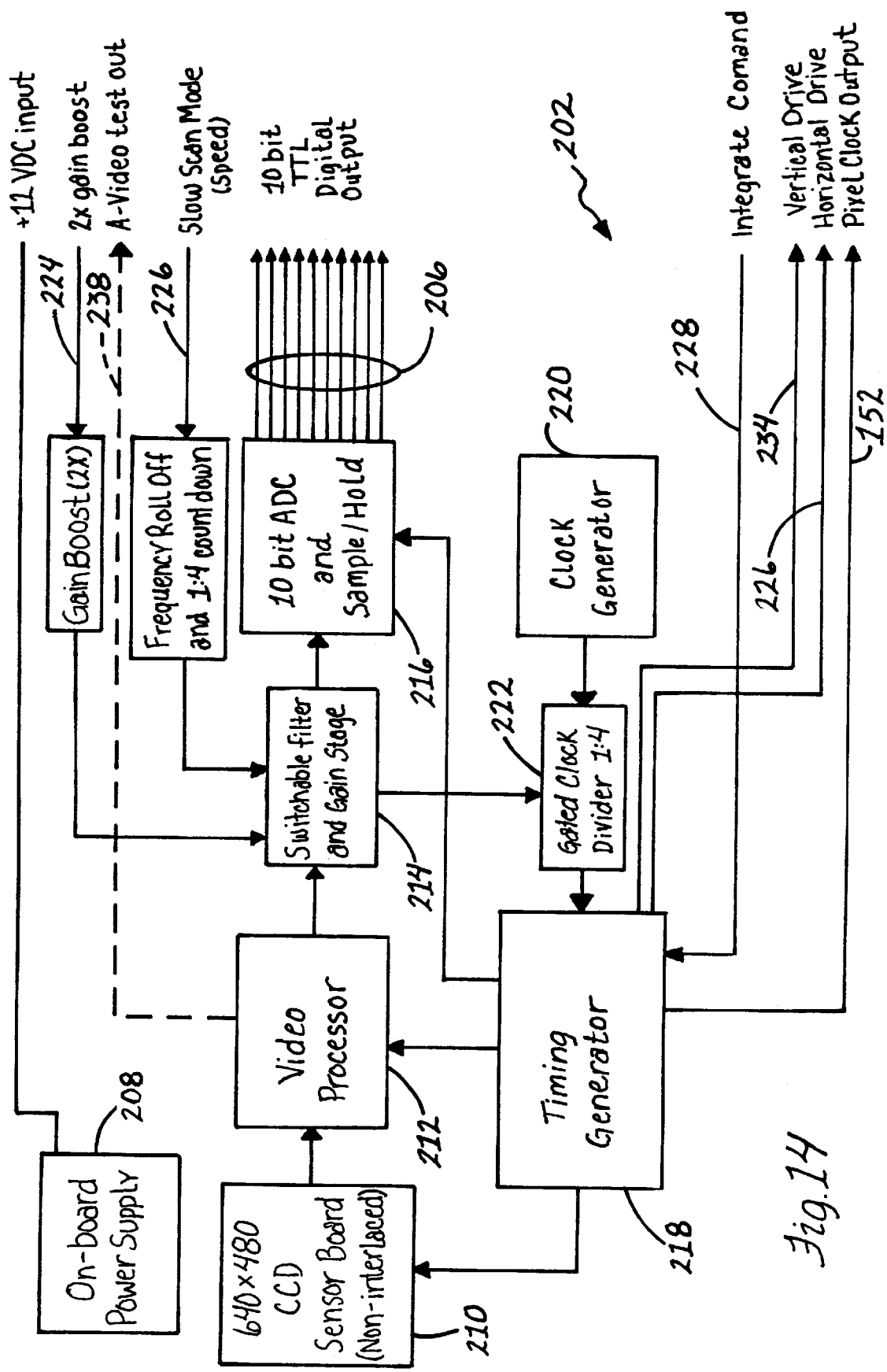
FIG. 14 shows a block diagram of the digital CCD camera subsystem of FIG. 13.

Turning now to FIG. 14, the digital camera 202, includes an on-board power supply to provide +12 volt DC for the camera 202 and the digital control board/transmission system 204. A COHU 6600 series camera is employed in which a 650×480 CCD sensor board 210 provides a non-interleaved output with a COHU progressive scan CCD Model 8710-9/001. The output of the sensor board 210 is provided to a video processor 212 which provides an optional analog video test output 238. A switchable filter and gain stage 214 provides CCD charge amplification, and a 10-bit ADC and sample and hold circuit 216 digitizes each pixel as the discrete pixels are read out and sampled. Accordingly, a timing generator 218 provides for master timing of the pixel clock 152, as well as vertical drive 234 and horizontal drive 236 signals. The timing generator 218 derives the timing signal from a clock generator 220 which may be divided back a gated clock divider 222 (1:4). Accordingly, the pixel clock 152 is used with the imager of the sensor board 210 in a progressive scan mode to provide a discrete pixel readout cycle. The sample and hold circuit samples the discrete pixel readout cycle in response to and correlated with the pixel clock, and ADC 216 provides a 10-bit TTL digital output to the digital control board/transmission system 204, described further in connection with FIG. 15.

The digital camera 202 also receives several input signals from the digital control board/transmission system 204, including gain, speed and integrate command signals. A gain signal 224 may be used at the digital camera 202 to provide a 2× gain boost at the switchable filter and gain stage 214 prior to the 10-bit digitization at ADC 216. Additionally, the speed signal 226 may be used to provide for a slow scan mode to provide frequency roll off and a 1:4 ratio of speed countdown with the gated clock driver 222 to reduce the speed of the clock provided to the timing generator 218. As discussed above, it may be advantageous to slow the clock of the CCD down to improve the noise associated with the discrete pixel readout from the imager of the sensor board 210 during the progressive scan mode.

Figure 15:
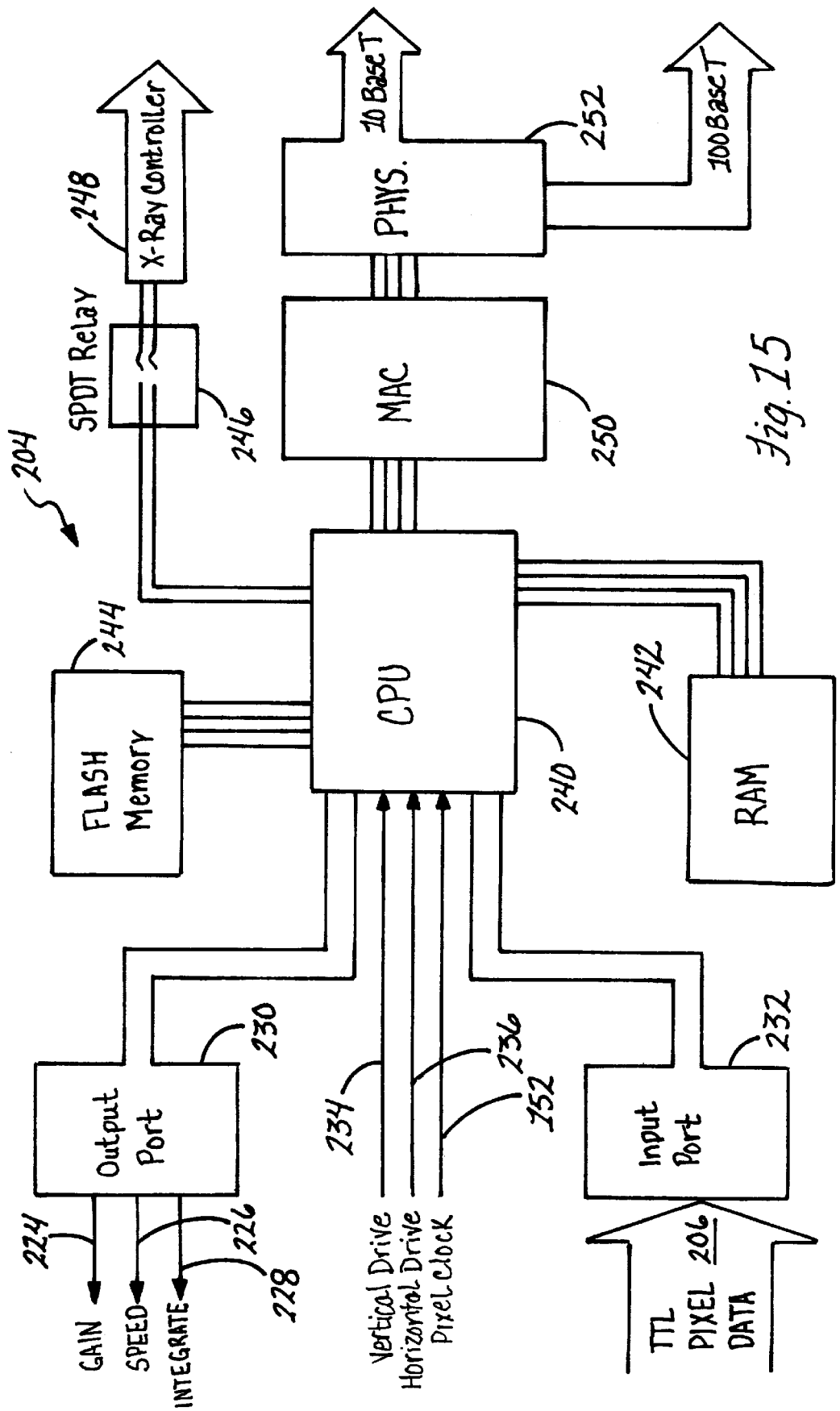
FIG. 15 is a block diagram showing the digital video transmission system controller board of FIG. 13.

FIG. 15 illustrates the digital control board/transmission system 204, which may also be referred to as a digital video transmission system provided as a controller board for interfacing the parallel output of the digital camera 202 to a serial data communications link. In the described embodiment an OTHICON NETARM microprocessor employing an ARM 7 processor provides input and output functions, data storage and processing for the controller board 204. Because of the power of the embedded 32 bit Reduced Instruction Set computer (RISC) in the DVT, the module 254 is capable of significant additional preprocessing of the video image data prior to transmission. A partial list of these processes include data compression, intensity look up tables to reduce of modify the number of bits used to digitize the image, bad pixel removal or correction, bad line removal or correction, dark current corrections, sensitivity corrections, general digital signal processing applications such as convolutions, grouping data into discrete packets and the normal error checking and re-transmission that is part of the ethernet protocols.

An output port 230 provides the gain 224, speed 226 and integrate 228 commands to the camera 202. The gain, speed and integrate commands are used with the camera 202 to facilitate integration of the charge signal at the CCD imager chip responsive to, e.g., the integrate signal 228 for allowing the X-ray image sensor with the sensor board 210 to integrate the sensed X-ray radiation pulses until a sufficient flux is integrated onto the imager 210 to provide a full scale output signal. Additionally, in input port 232 receives the 10-bit TTL pixel data 206 from the digital camera 202. The input port 232 may also be provided as a memory buffer or data register. Additionally, the controller 204 receives vertical drive 234 and horizontal drive 236 signals, as well as the pixel clock 152 from the digital camera 202. A central processing unit (CPU) 240 communicates with the digital camera 202 via the described input/output signals for receiving the discrete pixel readout signal.

A random access memory (RAM) 242 and a FLASH memory 244 are used by the CPU 240 for programming and data storage, which may be used for buffering digitized pixels received from the digital camera 202, so as to hold and retransmit video signals at predetermined transmission rates. A relay 246 is coupled to an X-ray controller 248 to allow the CPU 240 to communicate with and initiate operation of the X-ray source 12.

A media access controller (MAC) 250 is provided for use with the CPU 240 and a physical layer interface 252 providing a serial interface driver for transmitting the digitized pixels via the bi-directional serial communications link 190. As discussed, the physical interface 252 may be provided with any high speed serial interface such as a local area network, ethernet, telephone line or even a radio frequency communications channel.

While the invention herein disclosed has been described by means of specific embodiments and applications thereof, numerous modifications and variations could be made thereto by those skilled in the art without departing from the scope of the invention set forth in the claims.

What is claimed is:

1. A system for processing a digital image, comprising:
   means for generating a pixel clock;
   means for acquiring pixels responsive to said pixel clock generating means with a progressive scan of an image to provide a discrete pixel readout of the image digitizing each pixel as the discrete pixel readout is sampled;
   means for storing the digitized pixels in a buffer memory, wherein said means for generating the pixel clock provides a variable frequency pixel clock for said means for acquiring pixels for sampling and digitizing coherence of individual pixels for storing phase correlated pixels in the buffer memory; and
   means for serially transmitting the digitized pixels.

2. A system as recited in claim 1, comprising a data network for establishing a serial communications link from the buffer memory to a remote image processor.

3. A system as recited in claim 2, comprising a remote display controller for producing a digital image from the digitized pixels received at the image processor.

4. A pixel-correlated digital imaging system, comprising:
   a pixel clock generator;
   an imager operating in a progressive scan mode providing a discrete pixel readout cycle wherein said pixel clock generator provides a variable frequency pixel clock for operation of said imager in a mode in which the sampling and digitization of each individual pixel is phase correlated;
   a sample and hold circuit for sampling the discrete pixel readout responsive to said pixel clock;
   an analog to digital converter for digitizing each pixel as the discrete pixel readout is sampled;
   a buffer memory for storing digitized pixels received from said analog to digital converter;
   an image processor for generating an image from the digitized pixels;
   a serial communications link between said buffer memory and said image processor; and
   a serial interface driver for transmitting the digitized pixels to said image processor via said serial communications link.

5. A system as recited in claim 4, wherein said imager comprises a CCD camera.

6. A system as recited in claim 4, comprising a network server, wherein said serial communications link comprises a computer network and said image processor receives the digitized pixels via said computer network from said network server.

7. A system as recited in claim 4, wherein said serial communications link comprises a telephone line.

8. A system as recited in claim 4, wherein said analog to digital converter comprises a parallel output of approximately eight to twelve bits of resolution.

9. A system as recited in claim 4, wherein said serial communications link comprises a high speed twisted pair cable.

10. A pixel-correlated digital imaging system, comprising:
    a pixel clock generator;
    an imager comprising a CCD camera operating in a progressive scan mode providing a discrete pixel readout cycle;
    a sample and hold circuit for sampling the discrete pixel readout responsive to said pixel clock;
    an analog to digital converter for digitizing each pixel as the discrete pixel readout is sampled;
    a buffer memory for storing digitized pixels received from said analog to digital converter;
    an image processor for generating an image from the digitized pixels;
    a serial communications link between said buffer memory and said image processor;
    a serial interface driver for transmitting the digitized pixels to said image processor via said serial communications link;
    wherein said pixel clock generator provides a variable frequency pixel clock for operation of said CCD camera in a mode in which the sampling and digitization of each individual pixel is phase correlated.

11. A system as recited in claim 10, wherein said CCD camera comprises a digital video transmission module for organizing and transmitting digital data, and comprises a memory buffer for temporary storage of the digital data.

12. A system for processing a radioscopic image of an object under investigation, comprising:

an X-ray source configured to provide a sequence of X-ray radiation pulses directed at the object under investigation;

an X-ray image sensor configured to spatially sense the X-ray radiation pulses that pass through the object under investigation, said X-ray image sensor comprising a pixel clock generator, an imager operating in a progressive scan mode providing a discrete pixel readout cycle of sensed X-ray radiation pulses, a sample and hold circuit for sampling the discrete pixel readout responsive to said pixel clock, and an analog to digital converter for digitizing each pixel as the discrete pixel readout is sampled; and a controller for controlling said X-ray source and for acquiring digitized samples from said X-ray image sensor, said controller comprising a buffer memory for storing digitized pixels received from said analog to digital converter, and a serial interface driver for transmitting the digitized pixels.

13. A system as recited in claim 12, comprising an image processor receiving the digitized pixels transmitted by the serial interface driver of said controller for generating a radioscopic image from the digitized pixels.

14. A system as recited in claim 13, wherein said imager comprises an integrating CCD camera.

15. A system as recited in claim 14, wherein said CCD camera comprises a non-interlaced CCD imager chip.

16. A system as recited in claim 14, wherein said controller comprises bi-directional parallel to serial digital transmission circuitry.

17. A system as recited in claim 14, comprising a timing generator for generating said pixel clock and for maintaining coherence between said pixel clock and the digitizing of the pixels from the sampled discrete pixel readout at the analog to digital converter.

18. A system as recited in claim 17, wherein said controller generates an integrate signal, said integrating CCD imager chip being responsive to said integrate signal for allowing said X-ray image sensor to integrate the sensed X-ray radiation pulses until a sufficient flux is integrated onto said imager to provide a full scale output signal.

19. A system as recited in claim 17, wherein said controller generates a speed signal, said timing generator being responsive to said speed signal for changing the pixel clock of said X-ray image sensor to modify the scan rate of the discrete pixel readout cycle.

20. A method of processing a digital image, comprising the steps of:

generating a pixel clock signal;

acquiring pixels from a progressive scan of an image to provide a discrete pixel readout of the image;

sampling the discrete pixel readout responsive to the pixel clock signal;

digitizing each pixel as the discrete pixel readout is sampled;

storing the digitized pixels in a buffer memory;

establishing a serial communications link from the buffer memory to an image processor;

transmitting the digitized pixels to the image processor via the serial communications link; and producing a digital image from the digitized pixels received at the image processor; and integrating the acquired pixels from the progressive scan of the image until a sufficient flux is integrated to provide a full scale discrete pixel readout of the image.

21. A method of processing a digital image, comprising the steps of:

generating a pixel clock signal;

acquiring pixels from a progressive scan of an image to provide a discrete pixel readout of the image;

sampling the discrete pixel readout responsive to the pixel clock signal;

digitizing each pixel as the discrete pixel readout is sampled;

storing the digitized pixels in a buffer memory;

establishing a serial communications link from the buffer memory to an image processor;

transmitting the digitized pixels to the image processor via the serial communications link; and producing a digital image from the digitized pixels received at the image processor; and maintaining coherence between the generated pixel clock and the digitizing of the pixels from the sampled discrete pixel readout.

22. A method as recited in claim 21, comprising the step of organizing the digitized pixels for digital video transmission by using the buffer memory for temporary storage of digital data.

* * * * *